(12) United States Patent
Baker et al.

(10) Patent No.: US 7,700,574 B2
(45) Date of Patent: Apr. 20, 2010

(54) MODULATION OF RANKL EXPRESSION

(75) Inventors: Brenda F Baker, Carlsbad, CA (US); C. Frank Bennett, Carlsbad, CA (US); Kenneth W. Dobie, Del Mar, CA (US); Kathleen Myers, Oceanside, CA (US); Joshua Finger, San Marcos, CA (US); Lex M. Cowsert, San Mateo, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 759 days.

(21) Appl. No.: 10/944,274

(22) Filed: Sep. 17, 2004

(65) Prior Publication Data

US 2005/0148533 A1 Jul. 7, 2005

Related U.S. Application Data

(60) Provisional application No. 60/560,750, filed on Sep. 17, 2003.

(51) Int. Cl.
*A01N 43/04* (2006.01)
(52) U.S. Cl. .................... 514/44; 514/55; 435/455; 424/93.2
(58) Field of Classification Search .................... None
See application file for complete search history.

(56) References Cited

U.S. PATENT DOCUMENTS

| | | | | |
|---|---|---|---|---|
| 5,801,154 | A * | 9/1998 | Baracchini et al. | 514/44 |
| 5,985,664 | A | 11/1999 | Baker et al. | |
| 5,998,148 | A * | 12/1999 | Bennett et al. | 435/6 |
| 6,017,729 | A | 1/2000 | Anderson et al. | |
| 6,171,860 | B1 * | 1/2001 | Baker et al. | 435/375 |
| 6,242,213 | B1 | 6/2001 | Anderson | |
| 6,271,349 | B1 | 8/2001 | Dougall et al. | |
| 6,329,203 | B1 * | 12/2001 | Bennett et al. | 435/377 |
| 6,582,908 | B2 | 6/2003 | Fodor et al. | |
| 2001/0053519 | A1 | 12/2001 | Fodor et al. | |
| 2002/0159970 | A1 | 10/2002 | Choi et al. | |
| 2002/0182586 | A1 | 12/2002 | Morris et al. | |
| 2003/0017151 | A1 | 1/2003 | Dougall et al. | |
| 2003/0021785 | A1 | 1/2003 | Dougall | |
| 2003/0228597 | A1 | 12/2003 | Cowsert et al. | |

FOREIGN PATENT DOCUMENTS

| | | |
|---|---|---|
| JP | 2001157587 | 6/2001 |
| WO | WO 99/29865 | 6/1999 |
| WO | WO 01/23559 | 4/2001 |
| WO | WO 01/53486 | 7/2001 |
| WO | WO 02/16551 | 2/2002 |

OTHER PUBLICATIONS

Taylor, et al. Antisense oligonucleotides: a systematic high-throughput approach to target validation and gene function determination. Drug Discovery Today, v. 4, pp. 562-567 (1999).*
Trimarchi, et al. Disodium pamidronate for treating severe hypercalcemia in a hemodialysis patient. Nature Clinical Practice, v. 2, No. 8, pp. 459-463 (2006).*
Zaidi, et al. Osteoclastogenesis, bone resorption, and osteoclast-based therapeutics. Journal of Bone and Mineral Research, v. 18, No. 4, pp. 599-609 (2003).*
Lacey, et al. Osteoprotegerin ligand is a cytokine that regulates osteoclast differentiation and activation. Cell, v. 93, pp. 165-176 (1998).*
Hofbauer and Heufelder, Role of receptor activator of nuclear factor-kappaB ligand and osteoprotegerin in bone cell biology. Journal of Molecular Medicine, v. 79, Nos. 5-6, pp. 243-253 (2001).*
Asosingh, K. et al., 'The 5TMM series: a useful in vivo mouse model of human multiple myeloma,' *The Hematology Journal* (2000) 1, 351-356.
Anderson, D. M. et al., 'A homologue of the TNF receptor and its ligand enhance T-cell and dendritic-cell function,' Nature, vol. 390, Nov. 13, 1997, 175-179.
Burgess, T. L. et al., 'The Ligand for Osteoprotegerin (OPGL) Directly Activates Mature Osteoclasts,' *The Journal of Cell Biology*, vol. 145, No. 3, May 3, 1999, 527-538.
Durie, F. H. et al., 'Short Analytical Review, Collagen-Induced Arthritis as a Model of Rheumatoid Arthritis,' *Clinical Immunology and Immunopathology*, vol. 73, No. 1, Oct. 1994, 11-18.
Fata, J. E., et al., 'The Osteoclast Differentiation Factor Osteoprotegerin-Ligand Is Essential for Mammary Gland Development,' *Cell*, vol. 103, Sep. 29, 2000, 41-50.
Fuller, K. et al., 'TRANCE Is Necessary and Sufficient for Osteoblast-mediated Activation of Bone Resorption in Osteoclasts,' *J. Exp. Med.*, vol. 188, No. 5, Sep. 7, 1998, 997-1001.
Gori, F. et al., 'The Expression of Osteoprotegerin and RANK Ligand and the Support of Osteoclast Formation by Stromal-Osteoblast Lineage Cells Is Developmentally Regulated*,' *Endocrinology*, vol. 141, No. 12, 2000, 4768-4776.
Guise, T., 'Molecular Mechanisms of Osteolytic Bone Metastases,' © American Cancer Society 2000, Cancer Supplement, Jun. 15, 2000, vol. 88, No. 12, 2892-2898.
Hofbauer, L.C. et al.; Stimulation of Osteoprotegerin Ligand and Inhibition of Osteoprotegerin Production by Glucocorticoids in Human Osteoblastic Lineage Cells: Potential Paracrine Mechanisms of Glucocorticoid-Induced Osteoporosis*, *Endocrinology*, vol. 140, No. 10, 1999, 4382-4389.
Hsu, H. et al., 'Tumor necrosis factor receptor family member RANK mediates osteoclast differentiation and activation induced by osteoprotegerin ligand,'.*Proc. Natl. Acad. Sci, USA*, vol. 96, Mar. 1999, 3540-3545.
Itonaga, I. et al., Rheumatoid arthritis synovial macrophage-osteoclast differentiation is osteoprotegerin ligand-dependent, *Journal of Pathology*, 2000: 192, 97-104.
Kartsogiannis, V. et al., Localization of RANKL (Receptor Activator of NFkB Ligand) mRNA and Protein in Skeletal and Extraskeletal Tissues,*Bone*, vol. 25, No. 5, Nov. 1999, 525-534.

(Continued)

Primary Examiner—Richard Schnizer
Assistant Examiner—Jennifer Pitrak
(74) Attorney, Agent, or Firm—Isis Pharmaceuticals, Inc. Patent Dept.

(57) ABSTRACT

Compounds, compositions and methods are provided for modulating the expression of RANKL. The compositions comprise oligonucleotides, targeted to nucleic acid encoding RANKL. Methods of using these compounds for modulation of RANKL expression and for diagnosis and treatment of disease associated with expression of RANKL are provided.

16 Claims, No Drawings

OTHER PUBLICATIONS

Khosla, S., 'Minireview: The OPG/RANKL/RANK System,' *Endocrinology* 142 (12), Dec. 2001, 5050-5055.

Komarova, S.V., et al., 'Rank Ligand-induced Elevation of Cytosolic $Ca^{2+}$ Accelerates Nuclear Translocation of Nuclear Factor κB in Osteoclasts*,' *The Journal of Biological Chemistry*, vol. 278, No. 10, Mar. 7, 2003, 8286-8293.

Kong, Y. Y. et al., 'Osteoprotegerin ligand: a regulator of immune responses and bone physiology,' *Viewpoint Immunology Today*, vol. 21, No. 10, Oct. 2000, 495-502.

Kong, Y. Y. et al., 'Activated T cells regulate bone loss and joint destruction in adjuvant arthritis through osteoprotegerin ligand,' *Nature*, vol. 402, Nov. 18, 1999, 304-309.

Kong, Y. Y. et al., 'OPGL is a key regulator of osteoclastogenesis, lymphocyte development and lymph-node organogenesis,' Nature, vol. 397,Jan. 28, 1999, 315-323.

Lacey, D. L. et al., Osteoprotegerin Ligand Is a Cytokine that Regulates Osteoclast Differentiation and Activation, *Cell*, vol. 93, Apr. 17, 1998, 165-176.

Lee, S. K. and Lorenzo, J.A., 'Parathyroid Hormone Stimulates TRANCE and Inhibits Osteoprotegerin Messenger Ribonucleic Acid Expression in Murine Bone Marrow Cultures: Correlation with Osteoclast-Like Cell Formation*,' *Endocrinology*, vol. 140, No. 8, © 1999, 3552-3561.

Lum, Lawrence et al., 'Evidence for a Role of a Tumor Necrosis Factor-α (TNF-α)-Converting enzyme-like Protease in Shedding of TRANCE, a TNF Family Member Involved in Osteoclastogenesis and Dendritic Cell Survival*,' *The Journal of Biological Chemistry*, vol. 274, No. 19, May 7, 1999, 13613-13618.

Menaa, C. et al., 'Enhanced RANK ligand expression and responsivity of bone marrow cells in Paget's disease of bone,' *The Journal of Clinical Investigation*, vol. 105, No. 12, Jun. 2000, 1833-1838.

Nagai, M. et al., 'Cancer Cells Responsible for Humoral Hypercalcemia Express mRNA Encoding a Secreted Form of ODF/TRANCE That Induces Osteoclast Formation,' *Biochemical and Biophysical Research Communications* 269, No. 2, © 2000, 532-536.

Nakashima, T., 'RANKL and RANK as novel therapeutic targets for arthritis,' ISSN 1040-8711 © 2003 Lippincott Williams & Wilkins, 280-287.

Oyajobi, B. O. et al., 'Therapeutic Efficacy of a Soluble Receptor Activator of Nuclear Factor κB-IgG Fc Fusion Protein in suppressing Bone Resorption and Hypercalcemia in a Model of Humoral Hypercalcemia of Malignancy[1],' *Cancer Research* 61, Mar. 15, 2001, 2572-2578.

Pearse, R. N. et al., 'Multiple myeloma disrupts the TRANCE/osteoprotegerin cytokine axis to trigger bone destruction and promote tumor progression,' *PNAS*, vol. 98, No. 20, Sep. 25, 2001, 11581-11586.

Walsh, M.C. and Choi, Yongwon, 'Biology of the TRANCE axis,' *Cytokine & Growth Factor Reviews* 14, © 2003, 251-263.

Wang, R. et al., 'Regulation of activation-induced receptor activator of NF-κB ligand (RANKL) expression in T cells,' *Eur. J. Immunol.*, 2002, 32, 1090-1098.

Wong, B. R. et al., 'TRANCE (tumor Necrosis Factor [TNF]-related Activation-induced Cytokine), a New TNF Family Member Predominantly Expressed in T cells, Is a Dendritic Cell-specific Survival Factor,' *J. Exp. Med.*, vol. 186, No. 12, Dec. 15, 1997, 2075-2080.

Wong, B. R et al., 'TRANCE Is a Novel Ligand of the Tumor Necrosis Factor Receptor Family That Activates c-Jun N-terminal Kinase in T Cells*,' *The Journal of Biological Chemistry*, vol. 272, No. 40, Oct. 3, 1997, 25190-25194.

Yasuda, H. et al., Osteoclast differentiation factor is a ligand for osteoprotegerin/osteoclastogenesis-inhibitory factor and is identical to TRANCE/RANKL, *Proc. Natl. Aca. Sci. USA*, vol. 95, Mar. 1998, 3597-3602.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

New England BioLabs, Inc. Catalogue (1998): 121, 284.

Reynolds et al., Rational siRNA design for RNA interference, Mar. 2004, Nature Biotechnology, vol. 22, pp. 326-330.

Branch et al., "A good antisense molecule is hard to find," TIBS (1998) 23:45-50.

Crooke et al., "Basic Principles of Antisense Therapeutics" Antisense Research and Application (1998) Chapter 1:1-50.

Sanghvi et al., "Heterocyclic Base Modifications in Nucleic Acids and Their Applications in Antisense Oligonucleotides" Antisense Research and Applications (1993) pp. 273-288.

International Search Report from PCT/US2004/030736, dated Sep. 3, 2008.

* cited by examiner

SEQUENCE LISTING

```
<160> NUMBER OF SEQ ID NOS: 355

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                 20

<210> SEQ ID NO 2
```

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                              20

<210> SEQ ID NO 4
<211> LENGTH: 2271
<212> TYPE: DNA
<213> ORGANISM: H. sapiens
<220> FEATURE:
<220> FEATURE:
<221> NAME/KEY: CDS
<222> LOCATION: (185)...(1138)

<400> SEQUENCE: 4
aagcttggta ccgagctcgg atccactact cgacccacgc gtccgcgcgc cccaggagcc    60
aaagccgggc tccaagtcgg cgccccacgt cgaggctccg ccgcagcctc cggagttggc   120
cgcagacaag aaggggaggg agcgggagag ggaggagagc tccgaagcga gagggccgag   180 cgcc atg cgc cgc gcc agc aga gac tac acc aag tac ctg cgt ggc tcg   229
     Met Arg Arg Ala Ser Arg Asp Tyr Thr Lys Tyr Leu Arg Gly Ser
       1               5                  10                  15 gag gag atg ggc ggc ggc ccc gga gcc ccg cac gag ggc ccc ctg cac   277
Glu Glu Met Gly Gly Gly Pro Gly Ala Pro His Glu Gly Pro Leu His
                 20                  25                  30 gcc ccg ccg ccg cct gcg ccg cac cag ccc ccc gcc gcc tcc cgc tcc   325
Ala Pro Pro Pro Pro Ala Pro His Gln Pro Pro Ala Ala Ser Arg Ser
             35                  40                  45 atg ttc gtg gcc ctc ctg ggg ctg ggg ctg ggc cag gtt gtc tgc agc   373
Met Phe Val Ala Leu Leu Gly Leu Gly Leu Gly Gln Val Val Cys Ser
         50                  55                  60 gtc gcc ctg ttc ttc tat ttc aga gcg cag atg gat cct aat aga ata   421
Val Ala Leu Phe Phe Tyr Phe Arg Ala Gln Met Asp Pro Asn Arg Ile
 65                  70                  75 tca gaa gat ggc act cac tgc att tat aga att ttg aga ctc cat gaa   469
Ser Glu Asp Gly Thr His Cys Ile Tyr Arg Ile Leu Arg Leu His Glu
     80                  85                  90                  95 aat gca gat ttt caa gac aca act ctg gag agt caa gat aca aaa tta   517
Asn Ala Asp Phe Gln Asp Thr Thr Leu Glu Ser Gln Asp Thr Lys Leu
                100                 105                 110 ata cct gat tca tgt agg aga att aaa cag gcc ttt caa gga gct gtg   565
Ile Pro Asp Ser Cys Arg Arg Ile Lys Gln Ala Phe Gln Gly Ala Val
            115                 120                 125 caa aag gaa tta caa cat atc gtt gga tca cag cac atc aga gca gag   613
Gln Lys Glu Leu Gln His Ile Val Gly Ser Gln His Ile Arg Ala Glu
        130                 135                 140 aaa gcg atg gtg gat ggc tca tgg tta gat ctg gcc aag agg agc aag   661
Lys Ala Met Val Asp Gly Ser Trp Leu Asp Leu Ala Lys Arg Ser Lys
    145                 150                 155
```

```
ctt gaa gct cag cct ttt gct cat ctc act att aat gcc acc gac atc     709
Leu Glu Ala Gln Pro Phe Ala His Leu Thr Ile Asn Ala Thr Asp Ile
160                 165                 170                 175 cca tct ggt tcc cat aaa gtg agt ctg tcc tct tgg tac cat gat cgg     757
Pro Ser Gly Ser His Lys Val Ser Leu Ser Ser Trp Tyr His Asp Arg
            180                 185                 190 ggt tgg gcc aag atc tcc aac atg act ttt agc aat gga aaa cta ata     805
Gly Trp Ala Lys Ile Ser Asn Met Thr Phe Ser Asn Gly Lys Leu Ile
        195                 200                 205 gtt aat cag gat ggc ttt tat tac ctg tat gcc aac att tgc ttt cga     853
Val Asn Gln Asp Gly Phe Tyr Tyr Leu Tyr Ala Asn Ile Cys Phe Arg
    210                 215                 220 cat cat gaa act tca gga gac cta gct aca gag tat ctt caa cta atg     901
His His Glu Thr Ser Gly Asp Leu Ala Thr Glu Tyr Leu Gln Leu Met
225                 230                 235 gtg tac gtc act aaa acc agc atc aaa atc cca agt tct cat acc ctg     949
Val Tyr Val Thr Lys Thr Ser Ile Lys Ile Pro Ser Ser His Thr Leu
240                 245                 250                 255 atg aaa gga gga agc acc aag tat tgg tca ggg aat tct gaa ttc cat     997
Met Lys Gly Gly Ser Thr Lys Tyr Trp Ser Gly Asn Ser Glu Phe His
            260                 265                 270 ttt tat tcc ata aac gtt ggt gga ttt ttt aag tta cgg tct gga gag    1045
Phe Tyr Ser Ile Asn Val Gly Gly Phe Phe Lys Leu Arg Ser Gly Glu
        275                 280                 285 gaa atc agc atc gag gtc tcc aac ccc tcc tta ctg gat ccg gat cag    1093
Glu Ile Ser Ile Glu Val Ser Asn Pro Ser Leu Leu Asp Pro Asp Gln
    290                 295                 300 gat gca aca tac ttt ggg gct ttt aaa gtt cga gat ata gat tga        1138
Asp Ala Thr Tyr Phe Gly Ala Phe Lys Val Arg Asp Ile Asp
305                 310                 315 gccccagttt ttggagtgtt atgtatttcc tggatgtttg aaacatttt ttaaaacaag   1198
ccaagaaaga tgtatatagg tgtgtgagac tactaagagg catggcccca acggtacacg   1258
actcagtatc catgctcttg accttgtaga gaacacgcgt atttacagcc agtgggagat   1318
gttagactca tggtgtgtta cacaatggtt tttaaatttt gtaatgaatt cctagaatta   1378
aaccagattg gagcaattac gggttgacct tatgagaaac tgcatgtggg ctatgggagg   1438
ggttggtccc tggtcatgtg ccccttcgca gctgaagtgg agagggtgtc atctagcgca   1498
attgaaggat catctgaagg ggcaaattct tttgaattgt tacatcatgc tggaacctgc   1558
aaaaaatact ttttctaatg aggagagaaa atatatgtat ttttatataa tatctaaagt   1618
tatatttcag atgtaatgtt ttctttgcaa agtattgtaa attatatttg tgctatagta   1678
tttgattcaa aatatttaaa aatgtcttgc tgttgacata tttaatgttt taaatgtaca   1738
gacatattta actggtgcac tttgtaaatt ccctggggaa aacttgcagc taaggagggg   1798
aaaaaaatgt tgtttcctaa tatcaaatgc agtatatttc ttcgttcttt ttaagttaat   1858
agattttttc agacttgtca agcctgtgca aaaaaattaa aatggatgcc ttgaataata   1918
agcaggatgt tggccaccag gtgccttttca aatttagaaa ctaattgact ttagaaagct   1978
gacattgcca aaaggatac ataatgggcc actgaaatct gtcaagagta gttatataat   2038
tgttgaacag gtgttttttcc acaagtgccg caaattgtac ctttttttttt ttttcaaaat   2098
agaaaagtta ttagtggttt atcagcaaaa aagtccaatt ttaatttagt aaatgttatc   2158
ttatactgta caataaaaac attgcctttg aatgttaatt ttttggtaca aaaataaatt   2218
tatatgaaaa aaaaaaaaaa agggcggccg ctctagaggg ccctattcta tag         2271
```

<210> SEQ ID NO 5
<211> LENGTH: 30
<212> TYPE: DNA
<213> ORGANISM: Artificial Sequence
<220> FEATURE:
<223> OTHER INFORMATION: PCR Primer

<400> SEQUENCE: 5
cctagctaca gagtatcttc aactaatggt                                    30

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
tggtgcttcc tcctttcatc a                                             21

<210> SEQ ID NO 7
<211> LENGTH: 31
<212> TYPE: DNA
<213> ORGANISM: Artificial Sequence
<220> FEATURE:
<223> OTHER INFORMATION: PCR Probe

<400> SEQUENCE: 7
cgtcactaaa accagcatca aaatcccaag t                                  31

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                               20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                               20

<210> SEQ ID NO 11
<211> LENGTH: 2237
<212> TYPE: DNA
<213> ORGANISM: M. musculus
<220> FEATURE:
<220> FEATURE:

```
<221> NAME/KEY: CDS
<222> LOCATION: (142)...(1092)

<400> SEQUENCE: 11
cccacgtccc ggggagccac tgccaggacc tttgtgaacc ggtcggggcg ggggccgtgg      60
cggagtctgc tcggcggtgg gtggcccgag aagggagaga acgatcgcgg agcagggcgc     120
ccgaactccg ggcgccgcgc c atg cgc cgg gcc agc cga gac tac ggc aag       171
                        Met Arg Arg Ala Ser Arg Asp Tyr Gly Lys
                          1               5                  10 tac ctg cgc agc tcg gaa gag atg ggc agc ggc ccc ggc gtc cca cac       219
Tyr Leu Arg Ser Ser Glu Glu Met Gly Ser Gly Pro Gly Val Pro His
             15                  20                  25 gaa ggt ccg ctg cac ccc gcg cct tct gca ccg gct ccg gcg ccg cca       267
Glu Gly Pro Leu His Pro Ala Pro Ser Ala Pro Ala Pro Ala Pro Pro
 30                  35                  40 ccc gcc gcc tcc cgc tcc atg ttc ctg gcc ctc ctg ggg ctg gga ctg       315
Pro Ala Ala Ser Arg Ser Met Phe Leu Ala Leu Leu Gly Leu Gly Leu
         45                  50                  55 ggc cag gtg gtc tgc agc atc gct ctg ttc ctg tac ttt cga gcg cag       363
Gly Gln Val Val Cys Ser Ile Ala Leu Phe Leu Tyr Phe Arg Ala Gln
 60                  65                  70 atg gat cct aac aga ata tca gaa gac agc act cac tgc ttt tat aga       411
Met Asp Pro Asn Arg Ile Ser Glu Asp Ser Thr His Cys Phe Tyr Arg
 75                  80                  85                  90 atc ctg aga ctc cat gaa aac gca ggt ttg cag gac tcg act ctg gag       459
Ile Leu Arg Leu His Glu Asn Ala Gly Leu Gln Asp Ser Thr Leu Glu
             95                 100                 105 agt gaa gac aca cta cct gac tcc tgc agg agg atg aaa caa gcc ttt       507
Ser Glu Asp Thr Leu Pro Asp Ser Cys Arg Arg Met Lys Gln Ala Phe
         110                 115                 120 cag ggg gcc gtg cag aag gaa ctg caa cac att gtg ggg cca cag cgc       555
Gln Gly Ala Val Gln Lys Glu Leu Gln His Ile Val Gly Pro Gln Arg
     125                 130                 135 ttc tca gga gct cca gct atg atg gaa ggc tca tgg ttg gat gtg gcc       603
Phe Ser Gly Ala Pro Ala Met Met Glu Gly Ser Trp Leu Asp Val Ala
 140                 145                 150 cag cga ggc aag cct gag gcc cag cca ttt gca cac ctc acc atc aat       651
Gln Arg Gly Lys Pro Glu Ala Gln Pro Phe Ala His Leu Thr Ile Asn
155                 160                 165                 170 gct gcc agc atc cca tcg ggt tcc cat aaa gtc act ctg tcc tct tgg       699
Ala Ala Ser Ile Pro Ser Gly Ser His Lys Val Thr Leu Ser Ser Trp
             175                 180                 185 tac cac gat cga ggc tgg gcc aag atc tct aac atg acg tta agc aac       747
Tyr His Asp Arg Gly Trp Ala Lys Ile Ser Asn Met Thr Leu Ser Asn
         190                 195                 200 gga aaa cta agg gtt aac caa gat ggc ttc tat tac ctg tac gcc aac       795
Gly Lys Leu Arg Val Asn Gln Asp Gly Phe Tyr Tyr Leu Tyr Ala Asn
     205                 210                 215 att tgc ttt cgg cat cat gaa aca tcg gga agc gta cct aca gac tat       843
Ile Cys Phe Arg His His Glu Thr Ser Gly Ser Val Pro Thr Asp Tyr
 220                 225                 230 ctt cag ctg atg gtg tat gtc gtt aaa acc agc atc aaa atc cca agt       891
Leu Gln Leu Met Val Tyr Val Val Lys Thr Ser Ile Lys Ile Pro Ser
235                 240                 245                 250 tct cat aac ctg atg aaa gga ggg agc acg aaa aac tgg tcg ggc aat       939
Ser His Asn Leu Met Lys Gly Gly Ser Thr Lys Asn Trp Ser Gly Asn
             255                 260                 265 tct gaa ttc cac ttt tat tcc ata aat gtt ggg gga ttt ttc aag ctc       987
Ser Glu Phe His Phe Tyr Ser Ile Asn Val Gly Gly Phe Phe Lys Leu
```

```
                       270                  275                 280
cga gct ggt gaa gaa att agc att cag gtg tcc aac cct tcc ctg ctg   1035
Arg Ala Gly Glu Glu Ile Ser Ile Gln Val Ser Asn Pro Ser Leu Leu
            285                 290                 295 gat ccg gat caa gat gcg acg tac ttt ggg gct ttc aaa gtt cag gac   1083
Asp Pro Asp Gln Asp Ala Thr Tyr Phe Gly Ala Phe Lys Val Gln Asp
        300                 305                 310 ata gac tga gactcatttc gtggaacatt agcatggatg tcctagatgt ttggaaactt 1142
Ile Asp
315 cttaaaaaat ggatgatgtc tatacatgtg taagactact aagagacatg gcccacggtg   1202 tatgaaactc acagccctct ctcttgagcc ctgtacaggt tgtgtatatg taaagtccat   1262 aggtgatgtt agattcatgg tgattacaca acggttttac aattttgtaa tgatttccta   1322 gaattgaacc agattgggag aggtattccg atgcttatga aaacttaca cgtgagctat    1382 ggaagggggt cacagtctct ggtctaaccc ctggacatgt gccactgaga accttgaaat   1442 taagaggatg ccatgtcatt gcatagaaat gatagtgtga agggttaagt tcttttgaat   1502 tgttacattg cgctgggacc tgcaaataag ttcttttttt ctaatgagga gaaaaatata   1562 tgtattttta tataatgtct aaagttatat ttcaggtgta atgttttctg tgcaaagttt   1622 tgtaaattat atttgtgcta tagtatttga ttcaaaatat ttaaaaatgt ctcactgttg   1682 acatatttaa tgttttaaat gtacagatgt atttaactgg tgcactttgt aattcccctg   1742 aaggtactcg tagctaaggg ggcagaatac tgtttctggt gaccacatgt agtttatttc    1802 tttattcttt ttaacttaat agagtcttca gacttgtcaa aactatgcaa gcaaaataaa   1862 taaataaaaa taaatgaat accttgaata ataagtagga tgttggtcac caggtgcctt    1922 tcaaatttag aagctaattg actttaggag ctgacatagc caaaaggaa cataataggc     1982 tactgaaatc tgtcaggagt attatgcaa ttattgaaca ggtgtctttt tttacaagag    2042 ctacaaattg taaatttgg tttcttttttt ttcccataga aaatgtacta agtttatca     2102 gccaaaaaac aatccacttt ttaatttagt gaaagttatt ttattatact gtacaataaa   2162 agcattgtct ctgaatgtta attttttggt acaaaaata aatttgtacg aaaaaaaaaa    2222 aaaaaaaaaa aaaaa                                                    2237

<210> SEQ ID NO 12
<211> LENGTH: 19
<212> TYPE: DNA
<213> ORGANISM: Artificial Sequence
<220> FEATURE:
<223> OTHER INFORMATION: PCR Primer

<400> SEQUENCE: 12
tgcagcatcg ctctgttcc                                                  19

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
aagcagtgag tgctgtcttc tga                                             23

<210> SEQ ID NO 14
<211> LENGTH: 28
```

```
<212> TYPE: DNA
<213> ORGANISM: Artificial Sequence
<220> FEATURE:
<223> OTHER INFORMATION: PCR Probe

<400> SEQUENCE: 14
tttcgagcgc agatggatcc taacagaa                                      28

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                               20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                               20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                       27

<210> SEQ ID NO 18
<211> LENGTH: 957
<212> TYPE: DNA
<213> ORGANISM: R. norvegicus
<220> FEATURE:
<220> FEATURE:
<221> NAME/KEY: CDS
<222> LOCATION: (1)...(957)

<400> SEQUENCE: 18 atg cgc cgg gcc aac cga gac tac ggc aag tac ctg cgc ggc tcg gag    48
Met Arg Arg Ala Asn Arg Asp Tyr Gly Lys Tyr Leu Arg Gly Ser Glu
 1               5                  10                  15 gag atg ggc agt tgc cct ggc gtc cca cac gag ggt ccg ctg cat ccc    96
Glu Met Gly Ser Cys Pro Gly Val Pro His Glu Gly Pro Leu His Pro
             20                  25                  30 gcg cct tca gca ccg gct cca gcg ccg ccc ccc gcc gcc tcc cgc ttc   144
Ala Pro Ser Ala Pro Ala Pro Ala Pro Pro Pro Ala Ala Ser Arg Phe
         35                  40                  45 atg ttc ctg gcg ctc ctg ggg ctg gga ctg ggt cag gtg gtc tgc agc   192
Met Phe Leu Ala Leu Leu Gly Leu Gly Leu Gly Gln Val Val Cys Ser
     50                  55                  60 atc gct ctg ttc ctg tac ttt cga gcg cag atg gat cct aac aga ata   240
Ile Ala Leu Phe Leu Tyr Phe Arg Ala Gln Met Asp Pro Asn Arg Ile
 65                  70                  75                  80 tca gaa gac agc acg cgc tgc ttc tac aga att ctg aga ctc cgt gaa   288
Ser Glu Asp Ser Thr Arg Cys Phe Tyr Arg Ile Leu Arg Leu Arg Glu
```

```
aat aca ggt ttg cag gac tcg act ctg gag agc gaa gac aca gaa gca      336
Asn Thr Gly Leu Gln Asp Ser Thr Leu Glu Ser Glu Asp Thr Glu Ala
            100                 105                 110 cta cct gac tca tgc agg aga atg aaa caa gcc ttt caa ggg gcc gtg      384
Leu Pro Asp Ser Cys Arg Arg Met Lys Gln Ala Phe Gln Gly Ala Val
        115                 120                 125 caa agg gaa tta caa cac att gtg ggg cca cag cgc ttc tca gga gtt      432
Gln Arg Glu Leu Gln His Ile Val Gly Pro Gln Arg Phe Ser Gly Val
    130                 135                 140 cca gct atg atg gaa ggt tcg tgg ctc gat gtg gcc cgg cgg ggc aag      480
Pro Ala Met Met Glu Gly Ser Trp Leu Asp Val Ala Arg Arg Gly Lys
145                 150                 155                 160 cct gag gct cag ccg ttt gct cac ctc acc atc aat gct gcc gac atc      528
Pro Glu Ala Gln Pro Phe Ala His Leu Thr Ile Asn Ala Ala Asp Ile
                165                 170                 175 cca tcg ggt tcc cat aaa gtc agt ctg tcc tct tgg tac cat gat cga      576
Pro Ser Gly Ser His Lys Val Ser Leu Ser Ser Trp Tyr His Asp Arg
            180                 185                 190 ggc tgg gcc aag atc tct aac atg acg tta agc aac gga aaa cta agg      624
Gly Trp Ala Lys Ile Ser Asn Met Thr Leu Ser Asn Gly Lys Leu Arg
        195                 200                 205 gtt aac caa gat ggc ttc tat tac ctg tac gcc aac att tgc ttc agg      672
Val Asn Gln Asp Gly Phe Tyr Tyr Leu Tyr Ala Asn Ile Cys Phe Arg
    210                 215                 220 cat cat gaa acc tca ggg agc gta cct gcg gac tat ctt cag ctg atg      720
His His Glu Thr Ser Gly Ser Val Pro Ala Asp Tyr Leu Gln Leu Met
225                 230                 235                 240 gta tat gtc gtt aaa acc agc atc aaa atc cca agt tcg cat aac ctg      768
Val Tyr Val Val Lys Thr Ser Ile Lys Ile Pro Ser Ser His Asn Leu
                245                 250                 255 atg aaa ggg ggg agc act aag aac tgg tca ggg aat tct gaa ttc cac      816
Met Lys Gly Gly Ser Thr Lys Asn Trp Ser Gly Asn Ser Glu Phe His
            260                 265                 270 ttt tat tcc ata aac gtt gga gga ttt ttc aag ctc cgg gct ggt gag      864
Phe Tyr Ser Ile Asn Val Gly Gly Phe Phe Lys Leu Arg Ala Gly Glu
        275                 280                 285 gaa att agc gtc cag gtg tcc aac cct tcc ctg ttg gat ccg gat caa      912
Glu Ile Ser Val Gln Val Ser Asn Pro Ser Leu Leu Asp Pro Asp Gln
    290                 295                 300 gat gcg acg tac ttt ggg gct ttc aaa gtt caa gac ata gac tga           957
Asp Ala Thr Tyr Phe Gly Ala Phe Lys Val Gln Asp Ile Asp
305                 310                 315

957

<210> SEQ ID NO 19
<211> LENGTH: 25
<212> TYPE: DNA
<213> ORGANISM: Artificial Sequence
<220> FEATURE:
<223> OTHER INFORMATION: PCR Primer

<400> SEQUENCE: 19
tttattccat aaacgttgga ggatt                                           25

<210> SEQ ID NO 20
<211> LENGTH: 21
<212> TYPE: DNA
<213> ORGANISM: Artificial Sequence
<220> FEATURE:
<223> OTHER INFORMATION: PCR Primer
```

```
<400> SEQUENCE: 20
ttggacacct ggacgctaat t                                          21

<210> SEQ ID NO 21
<211> LENGTH: 22
<212> TYPE: DNA
<213> ORGANISM: Artificial Sequence
<220> FEATURE:
<223> OTHER INFORMATION: PCR Probe

<400> SEQUENCE: 21
ttcaagctcc gggctggtga gg                                         22

<210> SEQ ID NO 22
<211> LENGTH: 23
<212> TYPE: DNA
<213> ORGANISM: Artificial Sequence
<220> FEATURE:
<223> OTHER INFORMATION: PCR Primer

<400> SEQUENCE: 22
tgttctagag acagccgcat ctt                                        23

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
caccgacctt caccatcttg t                                          21

<210> SEQ ID NO 24
<211> LENGTH: 24
<212> TYPE: DNA
<213> ORGANISM: Artificial Sequence
<220> FEATURE:
<223> OTHER INFORMATION: PCR Probe

<400> SEQUENCE: 24
ttgtgcagtg ccagcctcgt ctca                                       24

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccgagctcgg taccaagctt                                            20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cggacgcgtg ggtcgagtag                                            20

<210> SEQ ID NO 27
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
cggccaactc cggaggctgc                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
ctcccgctcc ctcccttct                                           20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ctctcgcttc ggagctctcc                                          20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tggcgctcgg ccctctcgct                                          20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
cgcggcgcat ggcgctcggc                                          20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ctctgctggc gcggcgcatg                                          20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
```
gagccacgca ggtacttggt                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctggtgcggc gcaggcggcg                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cccagcccca ggagggccac                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
acgctgcaga caacctggcc                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
cgctctgaaa tagaagaaca                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tctgatattc tattaggatc                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
aaattctata aatgcagtga                              20

<210> SEQ ID NO 40
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 40
ttcatggagt ctcaaaattc                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gaaaatctgc attttcatgg                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
agagttgtgt cttgaaaatc                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cttgactctc cagagttgtg                                              20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gaatcaggta ttaattttgt                                              20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tctcctacat gaatcaggta                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
aggcctgttt aattctccta                                              20
```

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47 ttcctttgc acagctcctt                                            20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gatccaacga tatgttgtaa                                           20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ctttctctgc tctgatgtgc                                           20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
taaccatgag ccatccacca                                           20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gcttgctcct cttggccaga                                           20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
atgagcaaaa ggctgagctt                                           20

<210> SEQ ID NO 53
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 53
gatgtcggtg gcattaatag                                                   20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
actcacttta tgggaaccag                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
cgatcatggt accaagagga                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tgttggagat cttggcccaa                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
agttttccat tgctaaaagt                                                   20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ttaactatta gttttccatt                                                   20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
aaaagccatc ctgattaact                                                   20
```

```
<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
caaatgttgg catacaggta                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tgaagtttca tgatgtcgaa                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gatactctgt agctaggtct                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
agtgacgtac accattagtt                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
aacttgggat tttgatgctg                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cctcctttca tcagggtatg                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 66
ttccctgacc aatacttggt                                                20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
aatccaccaa cgtttatgga                                                20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
gacctcgatg ctgatttcct                                                20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tgttgcatcc tgatccggat                                                20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
tcgaacttta aaagccccaa                                                20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
catccaggaa atacataaca                                                20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tatacatctt tcttggcttg                                                20

<210> SEQ ID NO 73
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 73
atgcctctta gtagtctcac                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
aggtcaagag catggatact                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ctgtaaatac gcgtgttctc                                              20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
atgagtctaa catctcccac                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
aattcattac aaaatttaaa                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccaatctggt ttaattctag                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
```
ataaggtcaa cccgtaattg                                                  20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
catagcccac atgcagtttc                                                  20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
catgaccagg gaccaacccc                                                  20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctagatgaca ccctctccac                                                  20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ttcagatgat ccttcaattg                                                  20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
acaattcaaa agaatttgcc                                                  20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gcaggttcca gcatgatgta                                                  20

<210> SEQ ID NO 86
<211> LENGTH: 20
<212> TYPE: DNA
<213> ORGANISM: Artificial Sequence -continued

```
<220> FEATURE:
<223> OTHER INFORMATION: Antisense Oligonucleotide

<400> SEQUENCE: 86
atataacttt agatattata                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tttgcaaaga aaacattaca                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
agcacaaata taatttacaa                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ttaaatattt tgaatcaaat                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
acatttaaaa cattaaatat                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
tgcaccagtt aaatatgtct                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
ttttccccag ggaatttaca                                               20
```

```
<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gatattagga aacaacattt                                           20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gaagaaatat actgcatttg                                           20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
aagaacgaag aaatatactg                                           20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tattattcaa ggcatccatt                                           20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
cctggtggcc aacatcctgc                                           20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
tagtttctaa atttgaaagg                                           20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 99
caatgtcagc tttctaaagt                                           20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ttgacagatt tcagtggccc                                           20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gttcaacaat tatataacta                                           20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
actaataact tttctatttt                                           20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
aacatttact aaattaaaat                                           20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
aacattcaaa ggcaatgttt                                           20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
atccgagctc ggtaccaagc                                           20

<210> SEQ ID NO 106

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gcggacgcgt gggtcgagta                                               20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
agcccggctt tggctcctgg                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
ccggaggctg cggcggagcc                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ggccaactcc ggaggctgcg                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
cgcttcggag ctctcctccc                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
atggcgctcg gccctctcgc                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gcatggcgct cggccctctc                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
cggcgcatgg cgctcggccc                                               20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
tctctgctgg cgcggcgcat                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
catctcctcc gagccacgca                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
gggctggtgc ggcgcaggcg                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gaacatggag cgggaggcgg                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
tggcccagcc ccagccccag                                               20

<210> SEQ ID NO 119
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 119
cctggcccag ccccagcccc                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
atcttctgat attctattag                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
aaatgcagtg agtgccatct                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
gcacagctcc ttgaaaggcc                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tgagccatcc accatcgctt                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
catgagccat ccaccatcgc                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
aaccagatgg gatgtcggtg                                              20
```

```
<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
tggcccaacc ccgatcatgg                                        20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
tcgaaagcaa atgttggcat                                        20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
caatacttgg tgcttcctcc                                        20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
ggttggagac ctcgatgctg                                        20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
tgcatcctga tccggatcca                                        20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
atctatatct cgaactttaa                                        20

<210> SEQ ID NO 132
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 132
tcaatctata tctcgaactt                                         20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
ccaaacatcc aggaaataca                                         20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
tctttcttgg cttgttttaa                                         20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
ctgagtcgtg taccgttggg                                         20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
cccactggct gtaaatacgc                                         20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
cccgtaattg ctccaatctg                                         20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
caacccctcc catagcccac                                         20

```
<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
attgcgctag atgacaccct                                               20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
ccttcaattg cgctagatga                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
caaaagaatt tgccccttca                                               20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tctgaaatat aactttagat                                               20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
cattacatct gaaatataac                                               20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
tttgaatcaa atactatagc                                               20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 145
tctgtacatt taaaacatta                                          20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
acaaagtgca ccagttaaat                                          20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
tccccaggga atttacaaag                                          20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
agctgcaagt tttccccagg                                          20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cacaggcttg acaagtctga                                          20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
acctggtggc caacatcctg                                          20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
tctaaatttg aaaggcacct                                          20

<210> SEQ ID NO 152
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 152
agtggcccat tatgtatcct                                                 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
ggcacttgtg gaaaaacacc                                                 20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
ttttgctgat aaaccactaa                                                 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
gttcacaaag gtcctggcag                                                 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
gcagactccg ccacggcccc                                                 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
agcagactcc gccacggccc                                                 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
```

```
ccgccgagca gactccgcca                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
tgctccgcga tcgttctctc                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gccctgctcc gcgatcgttc                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
ccggcgcatg gcgcggcgcc                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
gctggcccgg cgcatggcgc                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
tcggctggcc cggcgcatgg                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
tctcggctgg cccggcgcat                                              20

<210> SEQ ID NO 165
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 165
ccttcgtgtg ggacgccggg                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
cgggaggcgg cgggtggcgg                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
acatggagcg ggaggcggcg                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
aacatggagc gggaggcggc                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
gctcgaaagt acaggaacag                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
tcttcactct ccagagtcga                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
cagttccttc tgcacggccc                                              20
```

```
<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
ggcttgcctc gctgggccac                                              20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
agcaaatgtt ggcgtacagg                                              20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
agctgaagat agtctgtagg                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ggattttgat gctggtttta                                              20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
tcagaattgc ccgaccagtt                                              20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
atgctaattt cttcaccagc                                              20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 178
tccggatcca gcagggaagg    20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
atgttccacg aaatgagtct    20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
gtcttacaca tgtatagaca    20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
tcatacaccg tgggccatgt    20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
accgttgtgt aatcaccatg    20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
gcatcggaat acctctccca    20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
tcagtggcac atgtccaggg    20

<210> SEQ ID NO 185

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
tgcaggtccc agcgcaatgt                                                   20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
cttatttgca ggtcccagcg                                                   20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187 cattcacct gaaatataac                                                    20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
aatcaaatac tatagcacaa                                                   20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
taaatatttt gaatcaaata                                                   20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
tgtcaacagt gagacatttt                                                   20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
```
gtacatttaa aacattaaat                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
tacaaagtgc accagttaaa                                              20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
agctacgagt accttcaggg                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
tttattttgc ttgcatagtt                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
aaggcacctg gtgaccaaca                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
tgaaaggcac ctggtgacca                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
cctgacagat ttcagtagcc                                              20

<210> SEQ ID NO 198
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 198
ggaaaaaaaa gaaaccaaaa                                                   20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
cagagacaat gcttttattg                                                   20

<210> SEQ ID NO 200
<211> LENGTH: 809
<212> TYPE: DNA
<213> ORGANISM: R. norvegicus
<220> FEATURE:
<220> FEATURE:
<221> NAME/KEY: CDS
<222> LOCATION: (1)...(164)

<400> SEQUENCE: 200 ggt cgg gca att ctg aat tcc act ttt att cca taa acg ttg gag gat        48
Gly Arg Ala Ile Leu Asn Ser Thr Phe Ile Pro  Thr Leu Glu Asp
  1               5                  10                  15 ttt tca agc tcc ggg ctg gtg agg aaa tta gcg tcc agg tgt cca acc        96
Phe Ser Ser Ser Gly Leu Val Arg Lys Leu Ala Ser Arg Cys Pro Thr
                 20                  25                  30 ctt ccc tgt tgg atc cgg atc aag atg cga cgt act ttg ggg ctt tca       144
Leu Pro Cys Trp Ile Arg Ile Lys Met Arg Arg Thr Leu Gly Leu Ser
             35                  40                  45 aag ttc aag aca tgg act ga  gacttgtttt gtggagcctt agcatggata           194
Lys Phe Lys Thr Trp Thr
     50 tgctagatgt ttggaaggtt cttaaaacat ggatgatgta gatacatgtg taagactact      254 aagagacgtg gcccacgttg tacaaaactc acggtcctct ctcgaccctg tacaggtcat      314 gtatatacaa agtccatagg ggatattaga ctcatggtga tcacacaatg gttttacaa       374 ttttgaaatg aattcctaga attaaaccaa attggaagag gtatacccat gcttataaaa      434 aaaatcgcat gtgagctatg gaagggtcat acatagtctc tgggtctaac tcctgggcct     494 gtgccactga gaacctcgaa attaagaggg taccgttaca ttgcagagaa atgatggttt      554 gaaaaggtaa gttcttttga attgttacat tgcgctggaa cctgcaaata agttcttttt     614 tctaatgagg agagaaaaat atatgaattt ttatataata tctaaagtta tatttcaggt     674 gtaaggtttt ctgtgcaaaa tattgtaaat tttatttggg ctatagtatt tgatcaaaaa     734 tatttaaaaa tgtctcactg ttgacatatt taatgtttta aatgtcaaga tgtatttaac     794 tggtgctctt tgtaa                                                      809

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201

```
ggcagcattg atggtgaggt                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
ggtacttgcc gtagtctcgg                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
gcgcaggtac ttgccgtagt                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
gcgatgctgc agaccacctg                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
acagagcgat gctgcagacc                                              20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
caggaacaga gcgatgctgc                                              20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
aagtacagga acagagcgat                                              20

<210> SEQ ID NO 208
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 208
ctcgaaagta caggaacaga                                              20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
ctgcgctcga aagtacagga                                              20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
tccatctgcg ctcgaaagta                                              20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
taggatccat ctgcgctcga                                              20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
tctgttagga tccatctgcg                                              20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
gatattctgt taggatccat                                              20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
cttctgatat tctgttagga                                              20
```

```
<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
cgcgtgctgt cttctgatat                                              20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
ttctgtagaa gcagcgcgtg                                              20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
tcacggagtc tcagaattct                                              20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
aacctgtatt ttcacggagt                                              20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
agtcgagtcc tgcaaacctg                                              20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
tccagagtcg agtcctgcaa                                              20

<210> SEQ ID NO 221
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 221
tttgcacggc cccttgaaag                                            20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
tgtaattccc tttgcacggc                                            20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
tgtggcccca caatgtgttg                                            20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
caaacggctg agcctcaggc                                            20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
gcagcattga tggtgaggtg                                            20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
actttatggg aacccgatgg                                            20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
agaggacaga ctgactttat                                            20
```

```
<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
tggtaccaag aggacagact                                               20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
gatcatggta ccaagaggac                                               20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
atcttggccc agcctcgatc                                               20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
tagagatctt ggcccagcct                                               20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
catgttagag atcttggccc                                               20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
agttttccgt tgcttaacgt                                               20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 234
acccttagtt ttccgttgct                                           20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
ggttaaccct tagttttccg                                           20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
atcttggtta acccttagtt                                           20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
aagccatctt ggttaaccct                                           20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
aatagaagcc atcttggtta                                           20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
taatagaagc catcttggtt                                           20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
caggtaatag aagccatctt                                           20

<210> SEQ ID NO 241
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 241
gcgtacaggt aatagaagcc                                              20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
tgttggcgta caggtaatag                                              20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
gcaaatgttg gcgtacaggt                                              20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
agatagtccg caggtacgct                                              20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
accatcagct gaagatagtc                                              20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
ttttaacgac atataccatc                                              20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
```

```
atgctggttt taacgacata                                           20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
cttgggattt tgatgctggt                                           20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
ccagttctta gtgctccccc                                           20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
aattcagaat tccctgacca                                           20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
taaaagtgga attcagaatt                                           20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
tggaataaaa gtggaattca                                           20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
cgcatcttga tccggatcca                                           20

<210> SEQ ID NO 254
<211> LENGTH: 20
<212> TYPE: DNA
<213> ORGANISM: Artificial Sequence
```

```
-continued

<220> FEATURE:
<223> OTHER INFORMATION: Antisense Oligonucleotide

<400> SEQUENCE: 254
agtacgtcgc atcttgatcc                                               20

<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
cccaaagtac gtcgcatctt                                               20

<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
aaagccccaa agtacgtcgc                                               20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
ctttgaaagc cccaaagtac                                               20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
tcagtctatg tcttgaactt                                               20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259
gcatatccat gctaaggctc                                               20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260
gtcttacaca tgtatctaca                                               20
```

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
cttagtagtc ttacacatgt                                       20

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 262
ttttgtacaa cgtgggccac                                       20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
gacctgtaca gggtcgagag                                       20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
ccattgtgtg atcaccatga                                       20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
tagacccaga gactatgtat                                       20

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
gtggcacagg cccaggagtt                                       20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
aggttctcag tggcacaggc                                            20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 268
ctctgcaatg taacggtacc                                            20

<210> SEQ ID NO 269
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
aaaccatcat ttctctgcaa                                            20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
acttatttgc aggttccagc                                            20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
gaaaacctta cacctgaaat                                            20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272
ttttgcacag aaaaccttac                                            20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273
ccagttaaat acatcttgac                                            20

<210> SEQ ID NO 274

```
<211> LENGTH: 20
<212> TYPE: DNA
<213> ORGANISM: M. musculus
<220> FEATURE:

<400> SEQUENCE: 274
ctgccaggac ctttgtgaac                                                 20

<210> SEQ ID NO 275
<211> LENGTH: 20
<212> TYPE: DNA
<213> ORGANISM: M. musculus
<220> FEATURE:

<400> SEQUENCE: 275
gggccgtggc ggagtctgct                                                 20

<210> SEQ ID NO 276
<211> LENGTH: 20
<212> TYPE: DNA
<213> ORGANISM: M. musculus
<220> FEATURE:

<400> SEQUENCE: 276
tggcggagtc tgctcggcgg                                                 20

<210> SEQ ID NO 277
<211> LENGTH: 20
<212> TYPE: DNA
<213> ORGANISM: M. musculus
<220> FEATURE:

<400> SEQUENCE: 277
gagagaacga tcgcggagca                                                 20

<210> SEQ ID NO 278
<211> LENGTH: 20
<212> TYPE: DNA
<213> ORGANISM: M. musculus
<220> FEATURE:

<400> SEQUENCE: 278
gaacgatcgc ggagcagggc                                                 20

<210> SEQ ID NO 279
<211> LENGTH: 20
<212> TYPE: DNA
<213> ORGANISM: M. musculus
<220> FEATURE:

<400> SEQUENCE: 279
gcgccatgcg ccgggccagc                                                 20

<210> SEQ ID NO 280
<211> LENGTH: 20
<212> TYPE: DNA
<213> ORGANISM: M. musculus
<220> FEATURE:

<400> SEQUENCE: 280
ccatgcgccg ggccagccga                                                 20

<210> SEQ ID NO 281
<211> LENGTH: 20
<212> TYPE: DNA
```

```
<213> ORGANISM: M. musculus
<220> FEATURE:

<400> SEQUENCE: 281
atgcgccggg ccagccgaga                                               20

<210> SEQ ID NO 282
<211> LENGTH: 20
<212> TYPE: DNA
<213> ORGANISM: M. musculus
<220> FEATURE:

<400> SEQUENCE: 282
ccgccacccg ccgcctcccg                                               20

<210> SEQ ID NO 283
<211> LENGTH: 20
<212> TYPE: DNA
<213> ORGANISM: M. musculus
<220> FEATURE:

<400> SEQUENCE: 283
cgccgcctcc cgctccatgt                                               20

<210> SEQ ID NO 284
<211> LENGTH: 20
<212> TYPE: DNA
<213> ORGANISM: M. musculus
<220> FEATURE:

<400> SEQUENCE: 284
gccgcctccc gctccatgtt                                               20

<210> SEQ ID NO 285
<211> LENGTH: 20
<212> TYPE: DNA
<213> ORGANISM: M. musculus
<220> FEATURE:

<400> SEQUENCE: 285
ctgttcctgt actttcgagc                                               20

<210> SEQ ID NO 286
<211> LENGTH: 20
<212> TYPE: DNA
<213> ORGANISM: M. musculus
<220> FEATURE:

<400> SEQUENCE: 286
tcgactctgg agagtgaaga                                               20

<210> SEQ ID NO 287
<211> LENGTH: 20
<212> TYPE: DNA
<213> ORGANISM: M. musculus
<220> FEATURE:

<400> SEQUENCE: 287
gggccgtgca gaaggaactg                                               20

<210> SEQ ID NO 288
<211> LENGTH: 20
<212> TYPE: DNA
<213> ORGANISM: M. musculus
<220> FEATURE:
```

```
<400> SEQUENCE: 288
gtggcccagc gaggcaagcc                                              20

<210> SEQ ID NO 289
<211> LENGTH: 20
<212> TYPE: DNA
<213> ORGANISM: M. musculus
<220> FEATURE:

<400> SEQUENCE: 289
cctgtacgcc aacatttgct                                              20

<210> SEQ ID NO 290
<211> LENGTH: 20
<212> TYPE: DNA
<213> ORGANISM: M. musculus
<220> FEATURE:

<400> SEQUENCE: 290
cctacagact atcttcagct                                              20

<210> SEQ ID NO 291
<211> LENGTH: 20
<212> TYPE: DNA
<213> ORGANISM: M. musculus
<220> FEATURE:

<400> SEQUENCE: 291
taaaaccagc atcaaaatcc                                              20

<210> SEQ ID NO 292
<211> LENGTH: 20
<212> TYPE: DNA
<213> ORGANISM: M. musculus
<220> FEATURE:

<400> SEQUENCE: 292
aactggtcgg gcaattctga                                              20

<210> SEQ ID NO 293
<211> LENGTH: 20
<212> TYPE: DNA
<213> ORGANISM: M. musculus
<220> FEATURE:

<400> SEQUENCE: 293
gctggtgaag aaattagcat                                              20

<210> SEQ ID NO 294
<211> LENGTH: 20
<212> TYPE: DNA
<213> ORGANISM: M. musculus
<220> FEATURE:

<400> SEQUENCE: 294
ccttccctgc tggatccgga                                              20

<210> SEQ ID NO 295
<211> LENGTH: 20
<212> TYPE: DNA
<213> ORGANISM: M. musculus
<220> FEATURE:

<400> SEQUENCE: 295
```
agactcattt cgtggaacat                                              20

<210> SEQ ID NO 296
<211> LENGTH: 20
<212> TYPE: DNA
<213> ORGANISM: M. musculus
<220> FEATURE:

<400> SEQUENCE: 296
tgtctataca tgtgtaagac                                              20

<210> SEQ ID NO 297
<211> LENGTH: 20
<212> TYPE: DNA
<213> ORGANISM: M. musculus
<220> FEATURE:

<400> SEQUENCE: 297
tgggagaggt attccgatgc                                              20

<210> SEQ ID NO 298
<211> LENGTH: 20
<212> TYPE: DNA
<213> ORGANISM: M. musculus
<220> FEATURE:

<400> SEQUENCE: 298
ccctggacat gtgccactga                                              20

<210> SEQ ID NO 299
<211> LENGTH: 20
<212> TYPE: DNA
<213> ORGANISM: M. musculus
<220> FEATURE:

<400> SEQUENCE: 299
acattgcgct gggacctgca                                              20

<210> SEQ ID NO 300
<211> LENGTH: 20
<212> TYPE: DNA
<213> ORGANISM: M. musculus
<220> FEATURE:

<400> SEQUENCE: 300
cgctgggacc tgcaaataag                                              20

<210> SEQ ID NO 301
<211> LENGTH: 20
<212> TYPE: DNA
<213> ORGANISM: M. musculus
<220> FEATURE:

<400> SEQUENCE: 301
ccctgaaggt actcgtagct                                              20

<210> SEQ ID NO 302
<211> LENGTH: 20
<212> TYPE: DNA
<213> ORGANISM: M. musculus
<220> FEATURE:

<400> SEQUENCE: 302
aactatgcaa gcaaaataaa                                              20

```
<210> SEQ ID NO 303
<211> LENGTH: 20
<212> TYPE: DNA
<213> ORGANISM: M. musculus
<220> FEATURE:

<400> SEQUENCE: 303
ggctactgaa atctgtcagg                                              20

<210> SEQ ID NO 304
<211> LENGTH: 20
<212> TYPE: DNA
<213> ORGANISM: R. norvegicus
<220> FEATURE:

<400> SEQUENCE: 304
ccgagactac ggcaagtacc                                              20

<210> SEQ ID NO 305
<211> LENGTH: 20
<212> TYPE: DNA
<213> ORGANISM: R. norvegicus
<220> FEATURE:

<400> SEQUENCE: 305
actacggcaa gtacctgcgc                                              20

<210> SEQ ID NO 306
<211> LENGTH: 20
<212> TYPE: DNA
<213> ORGANISM: R. norvegicus
<220> FEATURE:

<400> SEQUENCE: 306
caggtggtct gcagcatcgc                                              20

<210> SEQ ID NO 307
<211> LENGTH: 20
<212> TYPE: DNA
<213> ORGANISM: R. norvegicus
<220> FEATURE:

<400> SEQUENCE: 307
ggtctgcagc atcgctctgt                                              20

<210> SEQ ID NO 308
<211> LENGTH: 20
<212> TYPE: DNA
<213> ORGANISM: R. norvegicus
<220> FEATURE:

<400> SEQUENCE: 308
gcagcatcgc tctgttcctg                                              20

<210> SEQ ID NO 309
<211> LENGTH: 20
<212> TYPE: DNA
<213> ORGANISM: R. norvegicus
<220> FEATURE:

<400> SEQUENCE: 309
tcctgtactt tcgagcgcag                                              20
```

```
<210> SEQ ID NO 310
<211> LENGTH: 20
<212> TYPE: DNA
<213> ORGANISM: R. norvegicus
<220> FEATURE:

<400> SEQUENCE: 310
tcgagcgcag atggatccta                                               20

<210> SEQ ID NO 311
<211> LENGTH: 20
<212> TYPE: DNA
<213> ORGANISM: R. norvegicus
<220> FEATURE:

<400> SEQUENCE: 311
cgcagatgga tcctaacaga                                               20

<210> SEQ ID NO 312
<211> LENGTH: 20
<212> TYPE: DNA
<213> ORGANISM: R. norvegicus
<220> FEATURE:

<400> SEQUENCE: 312
atggatccta acagaatatc                                               20

<210> SEQ ID NO 313
<211> LENGTH: 20
<212> TYPE: DNA
<213> ORGANISM: R. norvegicus
<220> FEATURE:

<400> SEQUENCE: 313
atatcagaag acagcacgcg                                               20

<210> SEQ ID NO 314
<211> LENGTH: 20
<212> TYPE: DNA
<213> ORGANISM: R. norvegicus
<220> FEATURE:

<400> SEQUENCE: 314
agaattctga gactccgtga                                               20

<210> SEQ ID NO 315
<211> LENGTH: 20
<212> TYPE: DNA
<213> ORGANISM: R. norvegicus
<220> FEATURE:

<400> SEQUENCE: 315
actccgtgaa aatacaggtt                                               20

<210> SEQ ID NO 316
<211> LENGTH: 20
<212> TYPE: DNA
<213> ORGANISM: R. norvegicus
<220> FEATURE:

<400> SEQUENCE: 316
caggtttgca ggactcgact                                               20

<210> SEQ ID NO 317
<211> LENGTH: 20
```

```
<212> TYPE: DNA
<213> ORGANISM: R. norvegicus
<220> FEATURE:

<400> SEQUENCE: 317
ttgcaggact cgactctgga                                        20

<210> SEQ ID NO 318
<211> LENGTH: 20
<212> TYPE: DNA
<213> ORGANISM: R. norvegicus
<220> FEATURE:

<400> SEQUENCE: 318
ctttcaaggg gccgtgcaaa                                        20

<210> SEQ ID NO 319
<211> LENGTH: 20
<212> TYPE: DNA
<213> ORGANISM: R. norvegicus
<220> FEATURE:

<400> SEQUENCE: 319
caacacattg tggggccaca                                        20

<210> SEQ ID NO 320
<211> LENGTH: 20
<212> TYPE: DNA
<213> ORGANISM: R. norvegicus
<220> FEATURE:

<400> SEQUENCE: 320
ataaagtcag tctgtcctct                                        20

<210> SEQ ID NO 321
<211> LENGTH: 20
<212> TYPE: DNA
<213> ORGANISM: R. norvegicus
<220> FEATURE:

<400> SEQUENCE: 321
gatcgaggct gggccaagat                                        20

<210> SEQ ID NO 322
<211> LENGTH: 20
<212> TYPE: DNA
<213> ORGANISM: R. norvegicus
<220> FEATURE:

<400> SEQUENCE: 322
aggctgggcc aagatctcta                                        20

<210> SEQ ID NO 323
<211> LENGTH: 20
<212> TYPE: DNA
<213> ORGANISM: R. norvegicus
<220> FEATURE:

<400> SEQUENCE: 323
acgttaagca acggaaaact                                        20

<210> SEQ ID NO 324
<211> LENGTH: 20
<212> TYPE: DNA
<213> ORGANISM: R. norvegicus
```

```
<220> FEATURE:

<400> SEQUENCE: 324
agcaacggaa aactaagggt                                               20

<210> SEQ ID NO 325
<211> LENGTH: 20
<212> TYPE: DNA
<213> ORGANISM: R. norvegicus
<220> FEATURE:

<400> SEQUENCE: 325
cggaaaacta agggttaacc                                               20

<210> SEQ ID NO 326
<211> LENGTH: 20
<212> TYPE: DNA
<213> ORGANISM: R. norvegicus
<220> FEATURE:

<400> SEQUENCE: 326
aactaagggt taaccaagat                                               20

<210> SEQ ID NO 327
<211> LENGTH: 20
<212> TYPE: DNA
<213> ORGANISM: R. norvegicus
<220> FEATURE:

<400> SEQUENCE: 327
ggcttctatt acctgtacgc                                               20

<210> SEQ ID NO 328
<211> LENGTH: 20
<212> TYPE: DNA
<213> ORGANISM: R. norvegicus
<220> FEATURE:

<400> SEQUENCE: 328
ctattacctg tacgccaaca                                               20

<210> SEQ ID NO 329
<211> LENGTH: 20
<212> TYPE: DNA
<213> ORGANISM: R. norvegicus
<220> FEATURE:

<400> SEQUENCE: 329
acctgtacgc caacatttgc                                               20

<210> SEQ ID NO 330
<211> LENGTH: 20
<212> TYPE: DNA
<213> ORGANISM: R. norvegicus
<220> FEATURE:

<400> SEQUENCE: 330
gactatcttc agctgatggt                                               20

<210> SEQ ID NO 331
<211> LENGTH: 20
<212> TYPE: DNA
<213> ORGANISM: R. norvegicus
<220> FEATURE:
```

```
<400> SEQUENCE: 331
gatggtatat gtcgttaaaa                                              20

<210> SEQ ID NO 332
<211> LENGTH: 20
<212> TYPE: DNA
<213> ORGANISM: R. norvegicus
<220> FEATURE:

<400> SEQUENCE: 332
accagcatca aaatcccaag                                              20

<210> SEQ ID NO 333
<211> LENGTH: 20
<212> TYPE: DNA
<213> ORGANISM: R. norvegicus
<220> FEATURE:

<400> SEQUENCE: 333
aagatgcgac gtactttggg                                              20

<210> SEQ ID NO 334
<211> LENGTH: 20
<212> TYPE: DNA
<213> ORGANISM: R. norvegicus
<220> FEATURE:

<400> SEQUENCE: 334
gcgacgtact ttggggcttt                                              20

<210> SEQ ID NO 335
<211> LENGTH: 20
<212> TYPE: DNA
<213> ORGANISM: R. norvegicus
<220> FEATURE:

<400> SEQUENCE: 335
gtactttggg gctttcaaag                                              20

<210> SEQ ID NO 336
<211> LENGTH: 20
<212> TYPE: DNA
<213> ORGANISM: R. norvegicus
<220> FEATURE:

<400> SEQUENCE: 336
aagttcaaga catagactga                                              20

<210> SEQ ID NO 337
<211> LENGTH: 20
<212> TYPE: DNA
<213> ORGANISM: R. norvegicus
<220> FEATURE:

<400> SEQUENCE: 337
gagccttagc atggatatgc                                              20

<210> SEQ ID NO 338
<211> LENGTH: 20
<212> TYPE: DNA
<213> ORGANISM: R. norvegicus
<220> FEATURE:

<400> SEQUENCE: 338
```

-continued tgtagataca tgtgtaagac                                            20

<210> SEQ ID NO 339
<211> LENGTH: 20
<212> TYPE: DNA
<213> ORGANISM: R. norvegicus
<220> FEATURE:

<400> SEQUENCE: 339
acatgtgtaa gactactaag                                            20

<210> SEQ ID NO 340
<211> LENGTH: 20
<212> TYPE: DNA
<213> ORGANISM: R. norvegicus
<220> FEATURE:

<400> SEQUENCE: 340
gtggcccacg ttgtacaaaa                                            20

<210> SEQ ID NO 341
<211> LENGTH: 20
<212> TYPE: DNA
<213> ORGANISM: R. norvegicus
<220> FEATURE:

<400> SEQUENCE: 341
ctctcgaccc tgtacaggtc                                            20

<210> SEQ ID NO 342
<211> LENGTH: 20
<212> TYPE: DNA
<213> ORGANISM: R. norvegicus
<220> FEATURE:

<400> SEQUENCE: 342
tcatggtgat cacacaatgg                                            20

<210> SEQ ID NO 343
<211> LENGTH: 20
<212> TYPE: DNA
<213> ORGANISM: R. norvegicus
<220> FEATURE:

<400> SEQUENCE: 343
aactcctggg cctgtgccac                                            20

<210> SEQ ID NO 344
<211> LENGTH: 20
<212> TYPE: DNA
<213> ORGANISM: R. norvegicus
<220> FEATURE:

<400> SEQUENCE: 344
gcctgtgcca ctgagaacct                                            20

<210> SEQ ID NO 345
<211> LENGTH: 20
<212> TYPE: DNA
<213> ORGANISM: R. norvegicus
<220> FEATURE:

<400> SEQUENCE: 345
ggtaccgtta cattgcagag                                            20

-continued

```
<210> SEQ ID NO 346
<211> LENGTH: 20
<212> TYPE: DNA
<213> ORGANISM: R. norvegicus
<220> FEATURE:

<400> SEQUENCE: 346
ttgcagagaa atgatggttt                                               20

<210> SEQ ID NO 347
<211> LENGTH: 20
<212> TYPE: DNA
<213> ORGANISM: R. norvegicus
<220> FEATURE:

<400> SEQUENCE: 347
gctggaacct gcaaataagt                                               20

<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348
tgctcagcga gtgtgccagc                                               20

<210> SEQ ID NO 349
<211> LENGTH: 25
<212> TYPE: DNA
<213> ORGANISM: Artificial Sequence
<220> FEATURE:
<223> OTHER INFORMATION: primer

<400> SEQUENCE: 349
tttattccat aaatgttggg ggatt                                         25

<210> SEQ ID NO 350
<211> LENGTH: 22
<212> TYPE: DNA
<213> ORGANISM: Artificial Sequence
<220> FEATURE:
<223> OTHER INFORMATION: primer

<400> SEQUENCE: 350
ttggacacct gaatgctaat tt                                            22

<210> SEQ ID NO 351
<211> LENGTH: 23
<212> TYPE: DNA
<213> ORGANISM: Artificial Sequence
<220> FEATURE:
<223> OTHER INFORMATION: probe

<400> SEQUENCE: 351
ttcaagctcc gagctggtga aga                                           23

<210> SEQ ID NO 352
<211> LENGTH: 18
<212> TYPE: DNA
<213> ORGANISM: Artificial Sequence
<220> FEATURE:
<223> OTHER INFORMATION: primer

<400> SEQUENCE: 352
```

```
caaccttcc ctgctgga                                                      18

<210> SEQ ID NO 353
<211> LENGTH: 26
<212> TYPE: DNA
<213> ORGANISM: Artificial Sequence
<220> FEATURE:
<223> OTHER INFORMATION: primer

<400> SEQUENCE: 353
cagtctatgt cctgaacttt gaaagc                                            26

<210> SEQ ID NO 354
<211> LENGTH: 26
<212> TYPE: DNA
<213> ORGANISM: Artificial Sequence
<220> FEATURE:
<223> OTHER INFORMATION: probe

<400> SEQUENCE: 354
ccggatcaag atgcgacgta ctttgg                                            26

<210> SEQ ID NO 355
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 355
aggtgctcag gactccattt                                                   20
```

MODULATION OF RANKL EXPRESSION

CROSS REFERENCE TO RELATED APPLICATIONS

This application claims priority to U.S. provisional patent application No. 60/560,750, filed Sep. 17, 2003, which was converted from U.S. utility application originally assigned Ser. No. 10/665,279.

FIELD OF THE INVENTION

The present invention provides compositions and methods for modulating the expression of RANKL. In particular, this invention relates to compounds, particularly oligonucleotide compounds, which, in preferred embodiments, hybridize with nucleic acid molecules encoding RANKL. Such compounds are shown herein to modulate the expression of RANKL.

BACKGROUND OF THE INVENTION

Morphogenesis and remodeling of bone are accomplished by the coordinated actions of bone-resorbing osteoclasts and bone-forming osteoblasts, which metabolize and remodel bone structure throughout development and adult life. Bone is constantly being resorbed and formed at specific sites in the skeleton called basic multicellular units. An estimated 10% of the total bone mass in the human body is remodeled each year. Upon activation, osteoclasts, which differentiate from hematopoietic monocyte/macrophage precursors, migrate to the basic multicellular unit, resorb a portion of bone and finally undergo apoptosis. Subsequently, newly generated osteoblasts, arising from preosteoblastic/stromal cells, form bone at the site of resorption. The development of osteoclasts is controlled by preosteoblastic cells, so that the processes of bone resorption and formation are tightly coordinated, thus allowing for a wave of bone formation to follow each cycle of bone resorption. Imbalances between osteoclast and osteoblast activities can result in skeletal abnormalities characterized by decreased (osteoporosis) or increased (osteopetrosis) bone mass (Khosla, Endocrinology, 2001, 142, 5050-5055; Nakashima et al., Curr. Opin. Rheumatol., 2003, 15, 280-287).

Communication between osteoblasts and osteoclasts occurs through cytokines and cell-to-cell contacts. A cytokine that performs a key regulatory role in bone remodeling is receptor activator of NF-kappaB ligand (RANKL). RANKL was first identified as a tumor necrosis factor (TNF) superfamily member [also known as tumor necrosis-factor-related activation-induced cytokine (TRANCE), osteoprotegerin ligand (OPGL), and osteoclast differentiation factor (ODF) and tumor necrosis factor (ligand) superfamily member 11 (TNFSF11)] and was subsequently identified as a factor that is capable of inducing osteoclast differentiation in vitro (Anderson et al., Nature, 1997, 390, 175-179; Lacey et al., Cell, 1998, 93, 165-176; Wong et al., J. Exp. Med., 1997, 186, 2075-2080; Yasuda et al., Proc. Natl. Acad. Sci. USA, 1998, 95, 3597-3602). The human RANKL gene maps to chromosome 13q14. The highest expression levels of RANKL are found in bone, bone marrow and lymphoid tissues (Anderson et al., Nature, 1997, 390, 175-179; Lacey et al., Cell, 1998, 93, 165-176; Wong et al., J. Exp. Med., 1997, 186, 2075-2080; Yasuda et al., Proc. Natl. Acad. Sci. USA, 1998, 95, 3597-3602) and it can also be detected in brain, heart, kidney, skeletal muscle and skin (Kartsogiannis et al., Bone, 1999, 25, 525-534).

RANKL is assembled from three RANKL subunits to form the functional trimeric molecule. RANKL is initially anchored to the cell membrane, and a small fraction of the protein released from the cell surface by the proteolytic action of the metalloprotease-disintegrin TNF-alpha convertase (TACE) (Lum et al., J. Biol. Chem., 1999, 274, 13613-13618). RANKL is both necessary and sufficient to stimulate of osteoclast differentiation and activity as well as to inhibit osteoclast apoptosis (Fuller et al., J. Exp. Med., 1998, 188, 997-1001; Lacey et al., Cell, 1998, 93, 165-176; Lum et al., J. Biol. Chem., 1999, 274, 13613-13618; Yasuda et al., Proc. Natl. Acad. Sci. USA, 1998, 95, 3597-3602). RANKL is expressed on the surface of preosteoblastic and bone marrow stromal cells. Its expression can be positively or negatively modulated by various hormones, cytokines, growth factors and glucocorticoids, including, vitamin-D3, parathyroid hormone (PTH), interleukin 1-beta and TNF-alpha, all of which increase RANKL expression (Kong et al., Immunol. Today, 2000, 21, 495-502).

At the initiation of the cycle of bone resorption and formation, RANKL binds to its functional receptor RANK on preosteoclastic cells (Anderson et al., Nature, 1997, 390, 175-179; Lacey et al., Cell, 1998, 93, 165-176). This interaction between RANKL and RANK stimulates the formation of mature osteoclasts, which are phenotypically characterized by multinucleation, bone-resorbing function and expression of the lineage specific marker tartrate-resistant acid phosphatase (TRAP) (Burgess et al., J. Cell. Biol., 1999, 145, 527-538; Hsu et al., Proc. Natl. Acad. Sci. U.S.A., 1999, 96, 3540-3545; Lum et al., J. Biol. Chem., 1999, 274, 13613-13618; Yasuda et al., Proc. Natl. Acad. Sci. USA, 1998, 95, 3597-3602). Alternatively, RANKL can bind to the soluble receptor osteoprotegerin (OPG), which is expressed primarily by bone marrow stromal cells and serves to inhibit osteoclast maturation and activation by RANKL (Lacey et al., Cell, 1998, 93, 165-176; Yasuda et al., Proc. Natl. Acad. Sci. USA, 1998, 95, 3597-3602). PTH, a major regulator of bone remodeling, stimulates osteoclast function by simultaneously increasing RANKL expression while decreasing OPG expression (Lee and Lorenzo, Endocrinology, 1999, 140, 3552-3561). As preosteoblastic cells differentiate, RANKL mRNA levels are significantly reduced, whereas OPG mRNA levels increase (Gori et al., Endocrinology, 2000, 141, 4768-4776). Such a dynamic relationship between RANKL and OPG levels allows for a wave of osteoclast activity to be followed by a wave osteoblast activity, thereby completing the cycle of bone resorption and formation.

RANKL induces a transient elevation of calcium in osteoclasts due to release of calcium from intracellular stores (Komarova et al., J. Biol. Chem., 2003, 278, 8286-8293). In T-cells, T-cell receptor activation-induced calcium mobilization is solely responsible for the induction of RANKL expression (Wang et al., Eur. J. Immunol., 2002, 32, 1090-1098).

Mice homozygous for disruption of the RANKL gene are born at the expected frequency, but show severely retarded growth after weaning at three weeks of age. RANKL deficient mice exhibit severe osteopetrosis (thickening of bone), defects in tooth eruption and a complete lack of osteoclasts due to the inability of osteoblasts to support osteoclastogenesis (Kong et al., Immunol. Today, 2000, 21, 495-502).

RANKL function is not restricted to bone morphogenesis and remodeling. RANKL-deficient mice also display defects in early differentiation of T- and B-lymphocytes and lack all lymph nodes, demonstrating that RANKL is a regulator of lymph-node organogenesis and lymphocyte development, in addition to being an essential osteoclast differentiation factor (Kong et al., Immunol. Today, 2000, 21, 495-502). T-cell receptor stimulation induces RANKL gene expression, which subsequently leads to activation of c-Jun N-terminal kinase in T-cells (Wong et al., J. Biol. Chem., 1997, 272, 25190-25194). RANKL also participates in immune system function as an important survival factor for bone marrow derived dendritic cells by inhibiting apoptosis in these cells (Lum et al., J. Biol. Chem., 1999, 274, 13613-13618; Wong et al., J. Exp. Med., 1997, 186, 2075-2080). Additionally, RANKL is also required for the development of lobulo-alveolar mammary structures during pregnancy in mice (Fata et al., Cell, 2000, 103, 41-50).

Inappropriate activation of osteoclasts by RANKL can create an imbalance between the processes of bone resorption, resulting in the rate of bone resorption exceeding that of bone formation. Local or generalized bone loss is observed in many osteopenic disorders, including postmenopausal and age-related osteoporosis, periodontitis, familial expansile osteolysis and Paget's disease (Khosla, Endocrinology, 2001, 142, 5050-5055). Upregulation of RANKL mRNA has been reported in several of these diseases.

Paget's disease is characterized by large numbers of abnormal osteoclasts that induce increased bone resorption. RANKL mRNA expression is elevated in both cell lines and bone marrow derived from patients with Paget's disease. Furthermore, osteoclast precursors from Paget's disease patients undergo osteoclastogenesis at a much lower concentration of RANKL than normal cells (Menaa et al., J. Clin. Invest., 2000, 105, 1833-1838).

Other diseases with osteopenic pathologies, such as rheumatoid arthritis, chronic viral infection and adult and child leukemias, are characterized by activated T-cells and bone destruction (Kong et al., Immunol. Today, 2000, 21, 495-502). Rheumatoid arthritis is a chronic inflammatory disease characterized by progressive osteoclast-mediated bone resorption. Rheumatoid arthritis synovial fluid contains osteoclast precursors, RANKL-expressing T-cells and OPG-producing B-cells. Cultured macrophages from rheumatoid arthritis synovial fluid can differentiate into osteoclasts in a RANKL-dependent process (Itonaga et al., J. Pathol., 2000, 192, 97-104). In a T-cell dependent rat model of experimentally-induced arthritis that mimics many of the clinical features of human rheumatoid arthritis, inhibition of RANKL function through OPG treatment prevents bone destruction (Kong et al., Nature, 1999, 402, 304-309).

Multiple myeloma is a cancer in which osteoporosis and bone destruction are prominent features. Myeloma cell lines stimulate RANKL expression while inhibiting OPG expression by bone marrow stromal cells, resulting in a disruption of the balance between RANKL and OPG levels, followed by the aberrant production and activation of osteoclasts (Pearse et al., Proc. Natl. Acad. Sci. USA, 2001, 98, 11581-11586). A secreted form of RANKL is also expressed by cancer cells responsible for humoral hypercalcemia of malignancy (Nagai et al., Biochem. Biophys. Res. Commun., 2000, 269, 532-536). An increase in RANKL with a concurrent decrease in OPG expression is also observed following glucocorticoid treatment of osteoblastic lineage cells, which also stimulates osteoclastogenesis of these cells, suggesting a mechanism by which systemic glucocorticoid use leads to severe osteoporosis (Hofbauer et al., Endocrinology, 1999, 140, 4382-4389).

These findings demonstrate a link between immune function and bone physiology and also provide a molecular explanation for bone density loss associated with immune disorders and suggest that inhibition of RANKL function, and consequently osteoclast activity, can ameliorate osteopenic conditions (Kong et al., Immunol. Today, 2000, 21, 495-502).

Disclosed and claimed in the PCT publication WO 99/29865 are a nucleic acid molecule encoding human RANKL, antibodies that recognize RANKL polypeptides and cells modified to increase expression of RANKL polypeptides. Also disclosed and claimed is the modulation of an immune response in a mammal, wherein the modulator can be selected from a group consisting of antisense RANKL nucleic acid comprising at least one phosphodiester bond (Choi et al., 1999).

Disclosed in the U.S. Pat. No. 6,017,729 is a method for the isolation of a nucleic acid molecule encoding human RANKL, the nucleotide sequence encoding human RANKL and a method for the preparation of monoclonal antibodies that recognize RANKL (Anderson et al., 2000).

Disclosed and claimed in the PCT publication WO 01/53486 is a nucleic acid molecule having at least 80% nucleotide identity to a nucleic acid sequence encoding human RANKL, an antibody that binds to the polypeptide sequence encoded by a human RANKL nucleic acid molecule and the method of producing said antibody. Also disclosed and claimed is a method of inhibiting tumor cell growth by exposing tumor cells to an agent that inhibits the expression of polypeptide encoded by a human RANKL nucleic acid molecule, wherein the agent can be an antisense oligonucleotide that hybridizes to a RANKL nucleic acid molecule (Ashkenazi et al., 2001).

The PCT publication WO 01/23559 discloses and claims the nucleotide sequence containing a regulatory region of the human RANKL gene, as well as a method for identifying an antagonist to inhibit RANKL expression (Chandrasekhar et al., 2001).

The U.S. Pat. No. 6,271,349 discloses a method for the isolation of a nucleic acid molecule encoding RANKL, and a nucleotide sequence encoding human RANKL (Dougall and Galibert, 2001).

Disclosed and claimed in the U.S. Pat. No. 6,242,213 are a nucleic acid molecule encoding human RANKL, a host cell transformed or transfected with said nucleic acid molecule and a process of preparing RANKL polypeptide molecules. This publication also discloses that useful fragments of a RANKL nucleic acid molecule can include antisense or sense oligonucleotides (Anderson, 2001).

Disclosed and claimed in the U.S. pre-grant publication 20020159970 are a nucleic acid molecule encoding human RANKL, antibodies that recognize RANKL polypeptides and cells modified to increase expression of RANKL polypeptides. Also disclosed and claimed is a modulation of an immune response in a mammal, wherein the modulator can be selected from a group consisting of an antisense RANKL nucleic acid comprising at least one phosphodiester bond (Choi et al., 2002).

Disclosed the PCT publication WO 02/16551 are methods for treating a mammal having a disorder with a RANKL-inhibiting agent that is an antisense nucleic acid directed against RANKL RNA or with a RANKL-increasing agent that is a polypeptide (Choi et al., 2002).

The U.S. pre-grant publication 20020182586 discloses a method treating individuals with carcinoma cancer inhibitors which include antisense molecules that target a nucleic acid molecule encoding RANKL (Morris and Engelhard, 2002).

The U.S. pre-grant publication 20030017151 and the PCT publication WO 02/092016 disclose and claim a method of treating a patient with RANKL antisense oligonucleotides, an antibody that binds to a RANKL polypeptide or a ribozyme that cleaves RANKL mRNA to stimulate bone formation (Dougall and Anderson, 2003).

The U.S. pre-grant publication 20030021785 and the PCT publication WO 02/098362 disclose the use of an antisense approach to target RANKL mRNA transcripts (Dougall, 2003).

The Japanese patent application JP 2001157587 claims and discloses a nucleic acid sequences encoding human RANKL (Nagai, 2001).

As a consequence of RANKL involvement in many diseases, there remains a long felt need for additional agents capable of effectively regulating RANKL function. As such, inhibition is especially important in the treatment of disorders characterized by bone destruction, given that the upregulation of expression of RANKL is associated with so many different types of osteopenic diseases.

Antisense technology is emerging as an effective means for reducing the expression of specific gene products and has been proven to be uniquely useful in a number of therapeutic, diagnostic, and research applications.

The present invention provides compositions and methods for modulating RANKL expression, and consequently RANKL function.

SUMMARY OF THE INVENTION

The present invention is directed to compounds, especially nucleic acid and nucleic acid-like oligomers, which are targeted to a nucleic acid encoding RANKL, and which modulate the expression of RANKL. Pharmaceutical and other compositions comprising the compounds of the invention are also provided. Further provided are methods of screening for modulators of RANKL and methods of modulating the expression of RANKL in cells, tissues or animals comprising contacting said cells, tissues or animals with one or more of the compounds or compositions of the invention. Methods of treating an animal, particularly a human, suspected of having or being prone to a disease or condition associated with expression of RANKL are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding RANKL. This is accomplished by providing oligonucleotides that specifically hybridize with one or more nucleic acid molecules encoding RANKL.

As used herein, the terms "target nucleic acid" and "nucleic acid molecule encoding RANKL" have been used for convenience to encompass DNA encoding RANKL, RNA (including pre-mRNA and mRNA or portions thereof) transcribed from such DNA, and also cDNA derived from such RNA. A compound of this invention that hybridizes with its target nucleic acid is generally referred to an "antisense compound." Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which can be engaged in or facilitated by the RNA.

One preferred result of such interference with target nucleic acid function is modulation of the expression of RANKL. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which can be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention; "stringent conditions" under which compounds hybridize to a target sequence are determined by the nature and composition of the compounds and the assays in which they are being investigated.

"Complementary," as used herein, refers to the capacity for precise pairing between two nucleobases of a compound. For example, if a nucleobase at a certain position of a compound, e.g., an oligonucleotide, is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases that can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an antisense compound can hybridize over one or more segments such that intervening or adjacent segments are not involved in the hybridization event, e.g., a loop structure or hairpin structure is formed. It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted.

For example, an antisense compound in which 18 of 20 nucleobases of the antisense compound are complementary to a target region, and would therefore specifically hybridize, would have 90% complementarity to the target region of the target nucleic acid. In this example, the remaining non-complementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target region of the target nucleic acid and would thus fall within the scope of the present invention.

Percent complementarity of an antisense compound with a region of a target nucleic acid can be determined routinely using, e.g., BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity between the antisense compound and target region of the target nucleic acid is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some embodiments, homology, sequence identity or complementarity, is about 90%, about 92%, about 94%, about 95%, about 96%, about 97%, about 98%, or about 99%.

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds that hybridize to at least a portion, e.g., a region of the target nucleic acid. As such, these compounds can be introduced in the form of single-stranded, double-stranded, circular or hairpin oligomeric compounds and can contain structural elements such as internal or terminal bulges or loops.

Once introduced to a system, the compounds of the invention can elicit the action of one or more enzymes or structural proteins to effect modification of the target nucleic acid.

One non-limiting example of such an enzyme is RNAse H, a cellular endonuclease that cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing. Accordingly, in one embodiment of the invention, the antisense compound is a double stranded structure, e.g., a dsRNA.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs that are the potent inducers of RNAi (Tijsterman et al., *Science*, 2002, 295, 694-697).

The oligonucleotides of the present invention also include modified oligonucleotides in which a different base is present at one or more of the nucleotide positions in the oligonucleotide, as long as the structural and functional elements are maintained, e.g., the modified oligonucleotide hybridizes to and inhibits the expression of the target gene. For example, if the first nucleotide is an adenosine, modified oligonucleotides can be produced which contain thymidine, guanosine or cytidine at this position. This can be done at any of the positions of the oligonucleotide. These oligonucleotides are then tested using the methods described herein to determine their ability to inhibit expression of RANKL mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8-80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid can be, for example, a cellular gene (or mRNA transcribed from the gene) whose expression is associated with a particular disorder or disease state, or a nucleic acid molecule from an infectious agent. In the present invention, the target nucleic acid encodes RANKL.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes can have two or more alternative start codons, any one of which can be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding RANKL, regardless of the sequence(s) of such codons.

It is also known in the art that a translation termination codon (or "stop codon") of a gene can have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that can be targeted effectively with the antisense compounds of the present invention.

The open reading frame (ORF) or "coding region," which is known in the art to refer to the region between the translation initiation codon and the translation termination codon, is also a region which can be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, can also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop-position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are herein referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid that are accessible for hybridization.

While the specific sequences of certain preferred target segments are set forth herein, one of skill in the art will recognize that these serve to illustrate and describe particular embodiments within the scope of the present invention. Additional preferred target segments can be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric compounds are also targeted to or not targeted to regions of the target nucleobase sequence (e.g., such as those disclosed in Example 15) comprising nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, 2151-2200, 2201-2250, 2251-2271, or any combination thereof.

D. Screening and Target Validation

In a further embodiment, the "preferred target segments" identified herein can be employed in a screen for additional compounds that modulate the expression of RANKL. "Modulators" are those compounds that decrease or increase the expression of a nucleic acid molecule encoding RANKL and which comprise at least an 8-nucleobase portion that is complementary to a preferred target segment. The screening method comprises the steps of contacting a preferred target segment of a nucleic acid molecule encoding RANKL with one or more candidate modulators, and selecting for one or more candidate modulators which decrease or increase the expression of a nucleic acid molecule encoding RANKL. Once it is shown that the candidate modulator or modulators are capable of modulating (e.g. either decreasing or increasing) the expression of a nucleic acid molecule encoding RANKL, the modulator can then be employed in further investigative studies of the function of RANKL, or for use as a research, diagnostic, or therapeutic agent in accordance with the present invention.

The preferred target segments of the present invention can be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties can be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between RANKL and a disease state, phenotype, or condition. These methods include detecting or modulating RANKL comprising contacting a sample, tissue, cell, or organism with the compounds of the present invention, measuring the nucleic acid or protein level of RANKL and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The compounds of the invention are useful for research and diagnostics, because these compounds hybridize to nucleic acids encoding RANKL. For example, oligonucleotides that are shown to hybridize with such efficiency and under such conditions as disclosed herein as to be effective RANKL inhibitors will also be effective primers or probes under conditions favoring gene amplification or detection, respectively. These primers and probes are useful in methods requiring the specific detection of nucleic acid molecules encoding RANKL and in the amplification of said nucleic acid molecules for detection or for use in further studies of RANKL. Hybridization of the antisense oligonucleotides, particularly the primers and probes, of the invention with a nucleic acid encoding RANKL can be detected by means known in the art. Such means can include conjugation of an enzyme to the oligonucleotide, radiolabelling of the oligonucleotide or any other suitable detection means. Kits using such detection means for detecting the level of RANKL in a sample can also be prepared.

The specificity and sensitivity of antisense compounds is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder that can be treated by modulating the expression of RANKL is treated by administering antisense compounds in accordance with this invention. For example, in one non-limiting embodiment, the methods comprise the step of administering to the animal in need of treatment, a therapeutically effective amount of a RANKL inhibitor. The RANKL inhibitors of the present invention effectively inhibit the activity of the RANKL protein or inhibit the expression of the RANKL protein. In one embodiment, the activity or expression of RANKL in an animal is inhibited by about 10%. Preferably, the activity or expression of RANKL in an animal is inhibited by about 30%. More preferably, the activity or expression of RANKL in an animal is inhibited by 50% or more. Thus, the oligomeric compounds modulate expression of RANKL mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of RANKL can be measured in serum, adipose tissue, liver or any other body fluid, tissue or organ of the animal. Preferably, the cells contained within said fluids, tissues or organs being analyzed contain a nucleic acid molecule encoding RANKL protein and/or the RANKL protein itself.

The compounds of the invention can be utilized in pharmaceutical compositions by adding an effective amount of a compound to a suitable pharmaceutically acceptable diluent or carrier. Use of the compounds and methods of the invention can also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds can have internal nucleobase complementarity and can therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue that can be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages—Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides can also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other preferred oligonucleotides comprise one of the following at the 2' position: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification can be in the arabino (up) position or ribo (down) position. A preferred 2'-arabino modification is 2'-F. Similar modifications can also be made at other positions on the oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—CH$_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases can also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B. ed., CRC Press, 1993. Certain of these nucleobases are particularly useful for increasing the binding affinity of the compounds of the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention can also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications can be incorporated in a single compound or even at a single nucleoside within an oligonucleotide.

The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide can serve as a substrate for enzymes capable of cleaving RNA:DNA or RNA:RNA hybrids. By way of example, RNAse H is a cellular endonuclease that cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL, which cleaves both cellular and viral RNA. Cleavage of the RNA target can be routinely detected by gel electrophoresis and, if necessary, associated nucleic acid hybridization techniques known in the art.

Chimeric antisense compounds of the invention can be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention can also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations that include the antisense compounds of the invention. The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

Pharmaceutical compositions of the present invention include, but are not limited to, solutions, emulsions, foams and liposome-containing formulations. The pharmaceutical compositions and formulations of the present invention can comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions can contain additional components in addition to the dispersed phases, and the active drug that can be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term, which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention can also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers can be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention can be encapsulated within liposomes or can form complexes thereto, in particular to cationic liposomes. Alternatively, oligonucleotides can be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on Can 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. Preferred oral formulations are those in which oligonucleotides of the invention are administered in conjunction with one or more penetration enhancers, surfactants, and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention can be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed Jan. 20, 1999) and 10/071,822, filed Feb. 8, 2002, each of which is incorporated herein by reference in their entirety.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents can be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. Combinations of antisense compounds and other non-antisense drugs are also within the scope of this invention. Two or more combined compounds can be used together or sequentially.

In another related embodiment, compositions of the invention can contain one or more antisense compounds, particularly oligonucleotides, targeted to a first nucleic acid and one or more additional antisense compounds targeted to a second nucleic acid target. Alternatively, compositions of the invention can contain two or more antisense compounds targeted to different regions of the same nucleic acid target. Numerous examples of antisense compounds are known in the art. Two or more combined compounds can be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages can vary depending on the relative potency of individual oligonucleotides, and can generally be estimated based on $EC_{50}$s found to be effective in in vitro and in vivo animal models. In general, dosage is from 0.01 ug to 100 g per kg of body weight, and can be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it can be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank accession numbers, and the like recited in the present application are incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N-4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention can be conveniently and routinely made through the well-known technique of solid phase synthesis. Equipment for such synthesis is sold by several vendors including, for example, Applied Biosystems (Foster City, Calif.). Any other means for such synthesis known in the art can additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedicmethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group that has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support, but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand.*, 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.).

Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligo-nucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O- methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting RANKL

In accordance with the present invention, a series of nucleic acid duplexes comprising the antisense compounds of the present invention and their complements can be designed to target RANKL. The nucleobase sequence of the antisense strand of the duplex comprises at least a portion of an oligonucleotide in Table 1. The ends of the strands can be modified by the addition of one or more natural or modified nucleobases to form an overhang. The sense strand of the dsRNA is then designed and synthesized as the complement of the antisense strand and can also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine(dT) would have the following structure:

```
cgagaggcggacgggaccgTT    Antisense Strand
||||||||||||||||||||
TTgctctccgcctgccctggc    Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate RANKL expression using the assays described herein.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites. Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. Expression of the target can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells can be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

C2C12 Cells:

The mouse myoblast cell line was obtained from the American Type Culture Collection (ATCC) (Manassas, Va.). C2C12 cells were routinely cultured in DMEM, high glucose media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 24-well plates (Falcon-353047 at a density of ~10,000 cells/cm$^2$ for use in antisense oligonucleotide transfection.

UMR-106 Cells:

The rat osteosarcoma cell line was obtained from the American Type Culture Collection (ATCC) (Manassas, Va.). UMR-106 cells were routinely cultured in DMEM/F12 media (Invitrogen Corporation, Carlsbad, Calif.) supplemented with 10% fetal bovine serum (Invitrogen Corporation, Carlsbad, Calif.), 50 ug/ml Gentamicin Sulfate Solution (Irvine Scientific, Santa Ana, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded onto 24-well plates (Falcon-353047) at a density of ~5000 cells/cm$^2$ for use in antisense oligonucleotide transfection.

Primary Mouse Osteoblasts:

Primary mouse osteoblasts were prepared from calvaria of neonatal mice purchased from Charles River Laboratories. Primary mouse osteoblasts were routinely cultured in DMEM basal media (Invitrogen Corporation, Carlsbad, Calif.) supplemented with 10% fetal bovine serum (Invitrogen Corporation, Carlsbad, Calif.), 100 units per mL penicillin and 100 micrograms per mL streptomycin (Invitrogen Corporation, Carlsbad, Calif.). Cells were not passaged. Cells were seeded onto 6-well plates (Falcon-Primaria #353846) at a density of 50,000 cells/well for use in antisense oligonucleotide transfection.

Primary Mouse Bone Marrow-Derived Osteoclasts:

Primary mouse osteoclasts were prepared from the bone marrow of ~4-month old, female BALB/C mice purchased from Charles River Laboratories. Primary mouse bone marrow suspensions were routinely cultured in alpha-MEM media (Invitrogen Corporation, Carlsbad, Calif.) supplemented with 10% Fetal Bovine Serum (Cat #SH30071.03) (Hyclone, Logan, Utah), 50 ug/ml Gentamicin Sulfate Solution (Irvine Scientific, Santa Ana, Calif.), 50 ng/ml murine monocyte-colony stimulating factor (M-CSF) (R&D Systems, Minneapolis, Minn.) and 100 ng/ml soluble human receptor activator of NF-kB ligand (shRANKL) (Peprotech, Rocky Hill, N.J.). Cells were seeded onto 24-well plates (Falcon-353047) at a density of ~75,000 cells/cm$^2$ for use in antisense oligonucleotide transfection.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of RANKL Expression

Antisense modulation of RANKL expression can be assayed in a variety of ways known in the art. For example, RANKL mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of RANKL can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to RANKL can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of RANKL Inhibitors

Phenotypic Assays

Once RANKL inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of RANKL in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with RANKL inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the RANKL inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or RANKL inhibitor. Furthermore, to prevent the doctors from being biased in treatments, they are not informed as to whether the medication they are administering is a RANKL inhibitor or a placebo. Using this randomization approach, each volunteer has the same chance of being given either the new treatment or the placebo.

Volunteers receive either the RANKL inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding RANKL or RANKL protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and RANKL inhibitor treatment. In general, the volunteers treated with placebo have little or no response to treatment, whereas the volunteers treated with the RANKL inhibitor show positive trends in their disease state or condition index at the conclusion of the study.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates can be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps can be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of RANKL mRNA Levels

Quantitation of RANKL mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human RANKL were designed to hybridize to a human RANKL sequence, using published sequence information (GenBank accession number AF053712.1, incorporated herein as SEQ ID NO:4). For human RANKL the PCR primers were: forward primer: CCTAGCTACAGAGTATCTTCAACTAATGGT (SEQ ID NO: 5); reverse primer: TGGTGCTTCCTCCTTTCATCA (SEQ ID NO: 6) and the PCR probe was: FAM-CGTCAC-TAAAACCAGCATCAAAATCCCAAGT-TAMRA (SEQ ID NO: 7) where FAM is the fluorescent dye and TAMRA is the quencher dye. For human GAPDH the PCR primers were: forward primer: GAAGGTGAAGGTCGGAGTC (SEQ ID NO:8); reverse primer: GAAGATGGTGATGGGATTTC (SEQ ID NO:9); and the PCR probe was: 5' JOE-CAAGCT-TCCCGTTCTCAGCC-TAMRA 3' (SEQ ID NO: 10) where JOE is the fluorescent reporter dye and TAMRA is the quencher dye.

Probes and primers to mouse RANKL were designed to hybridize to a mouse RANKL sequence, using published sequence information (GenBank accession number AF013170.1, incorporated herein as SEQ ID NO:11). For mouse RANKL the PCR primers were: forward primer: TGCAGCATCGCTCTGTTCC (SEQ ID NO:12); reverse primer: AAGCAGTGAGTGCTGTCTTCTGA (SEQ ID NO: 13); and the PCR probe was: FAM-TTTCGAGCGCAGATG-GATCCTAACAGAA-TAMRA (SEQ ID NO: 14) where FAM is the fluorescent reporter dye and TAMRA is the quencher dye. For mouse GAPDH the PCR primers were: forward primer: GGCAAATTCAACGGCACAGT (SEQ ID NO:15); reverse primer: GGGTCTCGCTCCTGGAAGAT (SEQ ID NO:16) and the PCR probe was: 5' JOE-AAGGC-CGAGAATGGGAAGCTTGTCATC-TAMRA 3' (SEQ ID NO: 17) where JOE is the fluorescent reporter dye and TAMRA is the quencher dye.

Probes and primers to rat RANKL were designed to hybridize to a rat RANKL sequence, using published sequence information (GenBank accession number NM_057149.1, incorporated herein as SEQ ID NO:18). For rat RANKL the PCR primers were: forward primer: TTTAT-TCCATAAACGTTGGAGGATT (SEQ ID NO:19); reverse primer: TTGGACACCTGGACGCTAATT (SEQ ID NO: 20) and the PCR probe was: FAM-TTCAAGCTCCGGGCTG-GTGAGG-TAMRA; (SEQ ID NO: 21) where FAM is the fluorescent reporter dye and TAMRA is the quencher dye. For rat GAPDH the PCR primers were: forward primer: TGT-TCTAGAGACAGCCGCATCTT (SEQ ID NO:22); reverse primer: CACCGACCTTCACCATCTTGT (SEQ ID NO:23) and the PCR probe was: 5' JOE-TTGTGCAGTGCCAGC-CTCGTCTCA-TAMRA 3' (SEQ ID NO: 24) where JOE is the fluorescent reporter dye and TAMRA is the quencher dye.

Example 14

Northern Blot Analysis of RANKL mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human RANKL, a human RANKL specific probe was prepared by PCR using the forward primer CCTAGC-TACAGAGTATCTTCAACTAATGGT (SEQ ID NO: 5) and the reverse primer TGGTGCTTCCTCCTTTCATCA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse RANKL, a mouse RANKL specific probe was prepared by PCR using the forward primer TGCAG-CATCGCTCTGTTCC (SEQ ID NO: 12) and the reverse primer AAGCAGTGAGTGCTGTCTTCTGA (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

To detect rat RANKL, a rat RANKL specific probe was prepared by PCR using the forward primer TTTATTCCAT-AAACGTTGGAGGATT (SEQ ID NO: 12) and the reverse primer TTGGACACCTGGACGCTAATT (SEQ ID NO: 13). To normalize for variations in loading and transfer efficiency membranes were stripped and probed for rat glyceraldehyde-3-phosphate dehydrogenase (GAPDH) RNA (Clontech, Palo Alto, Calif.).

Example 15

Antisense Inhibition of Human RANKL Expression by Chimeric Phosphorothioate Oligonucleotides Having 2'-MOE Wings and a Deoxy Gap In accordance with the present invention, a series of antisense compounds was designed to target different regions of the human RANKL RNA, using published sequences (GenBank accession number AF053712.1, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds can be analyzed for their effect on human RANKL mRNA levels by quantitative real-time PCR as described in other examples herein.

TABLE 1

Inhibition of human RANKL mRNA levels by chimeric phosphorothioate oligonucleotides having 2'-MOE wings and a deoxy gap

| ISIS # | REGION | TARGET SEQ ID NO | TARGET SITE | SEQUENCE | SEQ ID NO |
|---|---|---|---|---|---|
| 109549 | 5'UTR | 4 | 1 | ccgagctcggtaccaagctt | 25 |
| 109550 | 5'UTR | 4 | 26 | cggacgcgtgggtcgagtag | 26 |
| 109551 | 5'UTR | 4 | 103 | cggccaactccggaggctgc | 27 |
| 109552 | 5'UTR | 4 | 129 | ctcccgctccctcccttct | 28 |
| 109553 | 5'UTR | 4 | 154 | ctctcgcttcggagctctcc | 29 |
| 109554 | Start Codon | 4 | 166 | tggcgctcggccctctcgct | 30 |
| 109555 | Start Codon | 4 | 175 | cgcggcgcatggcgctcggc | 31 |
| 109556 | Start Codon | 4 | 184 | ctctgctggcgcggcgcatg | 32 |
| 109557 | Coding | 4 | 209 | gagccacgcaggtacttggt | 33 |
| 109558 | Coding | 4 | 285 | ctggtgcggcgcaggcggcg | 34 |
| 109559 | Coding | 4 | 332 | cccagcccaggagggccac | 35 |
| 109560 | Coding | 4 | 356 | acgctgcagacaacctggcc | 36 |
| 109561 | Coding | 4 | 381 | cgctctgaaatagaagaaca | 37 |
| 109562 | Coding | 4 | 407 | tctgatattctattaggatc | 38 |
| 109563 | Coding | 4 | 436 | aaattctataaatgcagtga | 39 |
| 109564 | Coding | 4 | 450 | ttcatggagtctcaaaattc | 40 |
| 109565 | Coding | 4 | 463 | gaaaatctgcattttcatgg | 41 |
| 109566 | Coding | 4 | 476 | agagttgtgtcttgaaaatc | 42 |
| 109567 | Coding | 4 | 487 | cttgactctccagagttgtg | 43 |
| 109568 | Coding | 4 | 509 | gaatcaggtattaattttgt | 44 |
| 109569 | Coding | 4 | 519 | tctcctacatgaatcaggta | 45 |
| 109570 | Coding | 4 | 532 | aggcctgtttaattctccta | 46 |
| 109571 | Coding | 4 | 555 | ttccttttgcacagctcctt | 47 |
| 109572 | Coding | 4 | 575 | gatccaacgatatgttgtaa | 48 |
| 109573 | Coding | 4 | 598 | ctttctctgctctgatgtgc | 49 |
| 109574 | Coding | 4 | 621 | taaccatgagccatccacca | 50 |

TABLE 1-continued

Inhibition of human RANKL mRNA levels by
chimeric phosphorothioate oligonucleotides having
2'-MOE wings and a deoxy gap

| ISIS # | REGION | TARGET SEQ ID NO | TARGET SITE | SEQUENCE | SEQ ID NO |
|---|---|---|---|---|---|
| 109575 | Coding | 4 | 643 | gcttgctcctcttggccaga | 51 |
| 109576 | Coding | 4 | 666 | atgagcaaaaggctgagctt | 52 |
| 109577 | Coding | 4 | 690 | gatgtcggtggcattaatag | 53 |
| 109578 | Coding | 4 | 714 | actcactttatgggaaccag | 54 |
| 109579 | Coding | 4 | 737 | cgatcatggtaccaagagga | 55 |
| 109580 | Coding | 4 | 760 | tgttggagatcttggcccaa | 56 |
| 109581 | Coding | 4 | 782 | agttttccattgctaaaagt | 57 |
| 109582 | Coding | 4 | 791 | ttaactattagttttccatt | 58 |
| 109583 | Coding | 4 | 805 | aaaagccatcctgattaact | 59 |
| 109584 | Coding | 4 | 827 | caaatgttggcatacaggta | 60 |
| 109585 | Coding | 4 | 849 | tgaagtttcatgatgtcgaa | 61 |
| 109586 | Coding | 4 | 871 | gatactctgtagctaggtct | 62 |
| 109587 | Coding | 4 | 894 | agtgacgtacaccattagtt | 63 |
| 109588 | Coding | 4 | 919 | aacttgggattttgatgctg | 64 |
| 109589 | Coding | 4 | 941 | cctcctttcatcagggtatg | 65 |
| 109590 | Coding | 4 | 965 | ttccctgaccaatacttggt | 66 |
| 109591 | Coding | 4 | 1004 | aatccaccaacgtttatgga | 67 |
| 109592 | Coding | 4 | 1044 | gacctcgatgctgatttcct | 68 |
| 109593 | Coding | 4 | 1083 | tgttgcatcctgatccggat | 69 |
| 109594 | Coding | 4 | 1107 | tcgaactttaaaagccccaa | 70 |
| 109595 | 3'UTR | 4 | 1155 | catccaggaaatacataaca | 71 |
| 109596 | 3'UTR | 4 | 1195 | tatacatctttcttggcttg | 72 |
| 109597 | 3'UTR | 4 | 1222 | atgcctcttagtagtctcac | 73 |
| 109598 | 3'UTR | 4 | 1263 | aggtcaagagcatggatact | 74 |
| 109599 | 3'UTR | 4 | 1287 | ctgtaaatacgcgtgttctc | 75 |
| 109600 | 3'UTR | 4 | 1310 | atgagtctaacatctcccac | 76 |
| 109601 | 3'UTR | 4 | 1349 | aattcattacaaaatttaaa | 77 |
| 109602 | 3'UTR | 4 | 1370 | ccaatctggtttaattctag | 78 |
| 109603 | 3'UTR | 4 | 1392 | ataaggtcaacccgtaattg | 79 |
| 109604 | 3'UTR | 4 | 1414 | catagcccacatgcagtttc | 80 |
| 109605 | 3'UTR | 4 | 1437 | catgaccagggaccaacccc | 81 |
| 109606 | 3'UTR | 4 | 1475 | ctagatgacaccctctccac | 82 |
| 109607 | 3'UTR | 4 | 1497 | ttcagatgatccttcaattg | 83 |
| 109608 | 3'UTR | 4 | 1519 | acaattcaaaagaatttgcc | 84 |

TABLE 1-continued

Inhibition of human RANKL mRNA levels by chimeric phosphorothioate oligonucleotides having 2'-MOE wings and a deoxy gap

| ISIS # | REGION | TARGET SEQ ID NO | TARGET SITE | SEQUENCE | SEQ ID NO |
|---|---|---|---|---|---|
| 109609 | 3'UTR | 4 | 1539 | gcaggttccagcatgatgta | 85 |
| 109610 | 3'UTR | 4 | 1604 | atataactttagatattata | 86 |
| 109611 | 3'UTR | 4 | 1630 | tttgcaaagaaaacattaca | 87 |
| 109612 | 3'UTR | 4 | 1653 | agcacaaatataatttacaa | 88 |
| 109613 | 3'UTR | 4 | 1678 | ttaaatattttgaatcaaat | 89 |
| 109614 | 3'UTR | 4 | 1716 | acatttaaaacattaaatat | 90 |
| 109615 | 3'UTR | 4 | 1738 | tgcaccagttaaatatgtct | 91 |
| 109616 | 3'UTR | 4 | 1761 | ttttccccagggaatttaca | 92 |
| 109617 | 3'UTR | 4 | 1803 | gatattaggaaacaacattt | 93 |
| 109618 | 3'UTR | 4 | 1822 | gaagaaatatactgcatttg | 94 |
| 109619 | 3'UTR | 4 | 1828 | aagaacgaagaaatatactg | 95 |
| 109620 | 3'UTR | 4 | 1899 | tattattcaaggcatccatt | 96 |
| 109621 | 3'UTR | 4 | 1920 | cctggtggccaacatcctgc | 97 |
| 109622 | 3'UTR | 4 | 1942 | tagtttctaaatttgaaagg | 98 |
| 109623 | 3'UTR | 4 | 1966 | caatgtcagctttctaaagt | 99 |
| 109624 | 3'UTR | 4 | 2004 | ttgacagatttcagtggccc | 100 |
| 109625 | 3'UTR | 4 | 2027 | gttcaacaattatataacta | 101 |
| 109626 | 3'UTR | 4 | 2094 | actaataacttttctatttt | 102 |
| 109627 | 3'UTR | 4 | 2136 | aacatttactaaattaaaat | 103 |
| 109628 | 3'UTR | 4 | 2175 | aacattcaaaggcaatgttt | 104 |
| 181859 | 5'UTR | 4 | 3 | atccgagctcggtaccaagc | 105 |
| 181862 | 5'UTR | 4 | 27 | gcggacgcgtgggtcgagta | 106 |
| 181864 | 5'UTR | 4 | 52 | agcccggctttggctcctgg | 107 |
| 181866 | 5'UTR | 4 | 94 | ccggaggctgcggcggagcc | 108 |
| 181868 | 5'UTR | 4 | 102 | ggccaactccggaggctgcg | 109 |
| 181870 | 5'UTR | 4 | 150 | cgcttcggagctctcctccc | 110 |
| 181872 | Start Codon | 4 | 167 | atggcgctcggccctctcgc | 111 |
| 181874 | Start Codon | 4 | 169 | gcatggcgctcggccctctc | 112 |
| 181876 | Start Codon | 4 | 173 | cggcgcatggcgctcggccc | 113 |
| 181878 | Start Codon | 4 | 185 | tctctgctggcgcggcgcat | 114 |
| 181881 | Coding | 4 | 219 | catctcctccgagccacgca | 115 |
| 181883 | Coding | 4 | 288 | gggctggtgcggcgcaggcg | 116 |
| 181885 | Coding | 4 | 312 | gaacatggagcgggaggcgg | 117 |
| 181887 | Coding | 4 | 341 | tggcccagccccagccccag | 118 |

TABLE 1-continued

Inhibition of human RANKL mRNA levels by
chimeric phosphorothioate oligonucleotides having
2'-MOE wings and a deoxy gap

| ISIS # | REGION | TARGET SEQ ID NO | TARGET SITE | SEQUENCE | SEQ ID NO |
|---|---|---|---|---|---|
| 181889 | Coding | 4 | 343 | cctggcccagccccagcccc | 119 |
| 181891 | Coding | 4 | 411 | atcttctgatattctattag | 120 |
| 181893 | Coding | 4 | 427 | aaatgcagtgagtgccatct | 121 |
| 181895 | Coding | 4 | 547 | gcacagctccttgaaaggcc | 122 |
| 181897 | Coding | 4 | 615 | tgagccatccaccatcgctt | 123 |
| 181899 | Coding | 4 | 617 | catgagccatccaccatcgc | 124 |
| 181901 | Coding | 4 | 700 | aaccagatgggatgtcggtg | 125 |
| 181903 | Coding | 4 | 748 | tggcccaaccccgatcatgg | 126 |
| 181905 | Coding | 4 | 834 | tcgaaagcaaatgttggcat | 127 |
| 181907 | Coding | 4 | 956 | caatacttggtgcttcctcc | 128 |
| 181909 | Coding | 4 | 1051 | ggttggagacctcgatgctg | 129 |
| 181911 | Coding | 4 | 1080 | tgcatcctgatccggatcca | 130 |
| 181913 | Coding | 4 | 1116 | atctatatctcgaactttaa | 131 |
| 181915 | Stop Codon | 4 | 1119 | tcaatctatatctcgaactt | 132 |
| 181917 | 3'UTR | 4 | 1160 | ccaaacatccaggaaataca | 133 |
| 181919 | 3'UTR | 4 | 1189 | tctttcttggcttgttttaa | 134 |
| 181921 | 3'UTR | 4 | 1245 | ctgagtcgtgtaccgttggg | 135 |
| 181923 | 3'UTR | 4 | 1295 | cccactggctgtaaatacgc | 136 |
| 181925 | 3'UTR | 4 | 1382 | cccgtaattgctccaatctg | 137 |
| 181927 | 3'UTR | 4 | 1424 | caaccccctcccatagcccac | 138 |
| 181930 | 3'UTR | 4 | 1481 | attgcgctagatgacaccct | 139 |
| 181932 | 3'UTR | 4 | 1487 | ccttcaattgcgctagatga | 140 |
| 181934 | 3'UTR | 4 | 1513 | caaaagaatttgccccttca | 141 |
| 181936 | 3'UTR | 4 | 1610 | tctgaaatataactttagat | 142 |
| 181938 | 3'UTR | 4 | 1617 | cattacatctgaaatataac | 143 |
| 181940 | 3'UTR | 4 | 1670 | tttgaatcaaatactatagc | 144 |
| 181942 | 3'UTR | 4 | 1721 | tctgtacatttaaaacatta | 145 |
| 181944 | 3'UTR | 4 | 1744 | acaaagtgcaccagttaaat | 146 |
| 181946 | 3'UTR | 4 | 1758 | tccccagggaatttacaaag | 147 |
| 181948 | 3'UTR | 4 | 1770 | agctgcaagttttccccagg | 148 |
| 181950 | 3'UTR | 4 | 1867 | cacaggcttgacaagtctga | 149 |
| 181952 | 3'UTR | 4 | 1921 | acctggtggccaacatcctg | 150 |
| 181954 | 3'UTR | 4 | 1937 | tctaaatttgaaaggcacct | 151 |
| 181956 | 3'UTR | 4 | 1992 | agtggcccattatgtatcct | 152 |

TABLE 1-continued

Inhibition of human RANKL mRNA levels by chimeric phosphorothioate oligonucleotides having 2'-MOE wings and a deoxy gap

| ISIS # | REGION | TARGET SEQ ID NO | TARGET SITE | SEQUENCE | SEQ ID NO |
|---|---|---|---|---|---|
| 181958 | 3'UTR | 4 | 2048 | ggcacttgtggaaaaacacc | 153 |
| 181960 | 3'UTR | 4 | 2109 | ttttgctgataaaccactaa | 154 |

Example 16

Antisense Inhibition of Mouse RANKL Expression by Chimeric Phosphorothioate Oligonucleotides Having 2'-MOE Wings and a Deoxy Gap In accordance with the present invention, a second series of antisense compounds was designed to target different regions of the mouse RANKL RNA, using published sequences (GenBank accession number AF013170.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse RANKL mRNA levels by quantitative real-time PCR as described in other examples herein. Data are averages from three experiments in which C2C12 cells were treated with the antisense oligonucleotides of the present invention. If present, "N.D." indicates "no data".

TABLE 2

Inhibition of mouse RANKL mRNA levels by chimeric phosphorothioate oligonucleotides having 2'-MOE wings and a deozy gap

| ISIS # | REGION | TARGET SEQ ID NO | TARGET SITE | SEQUENCE | % INHIB | SEQ ID NO |
|---|---|---|---|---|---|---|
| 180788 | 5'UTR | 11 | 20 | gttcacaaaggtcctggcag | 62 | 155 |
| 180789 | 5'UTR | 11 | 51 | gcagactccgccacggcccc | 34 | 156 |
| 180790 | 5'UTR | 11 | 52 | agcagactccgccacggccc | 59 | 157 |
| 180791 | 5'UTR | 11 | 58 | ccgccgagcagactccgcca | 44 | 158 |
| 180792 | 5'UTR | 11 | 95 | tgctccgcgatcgttctctc | 77 | 159 |
| 180793 | 5'UTR | 11 | 99 | gccctgctccgcgatcgttc | 74 | 160 |
| 180794 | Start Codon | 11 | 131 | ccggcgcatggcgcggcgcc | 0 | 161 |
| 180795 | Start Codon | 11 | 137 | gctggcccggcgcatggcgc | 62 | 162 |
| 180796 | Start Codon | 11 | 140 | tcggctggcccggcgcatgg | 67 | 163 |
| 180797 | Start Codon | 11 | 142 | tctcggctggcccggcgcat | 60 | 164 |
| 180798 | Coding | 11 | 205 | ccttcgtgtgggacgccggg | 34 | 165 |
| 180799 | Coding | 11 | 262 | cgggaggcggcgggtggcgg | 52 | 166 |
| 180800 | Coding | 11 | 270 | acatggagcgggaggcggcg | 54 | 167 |
| 180801 | Coding | 11 | 271 | aacatggagcgggaggcggc | 40 | 168 |
| 180802 | Coding | 11 | 340 | gctcgaaagtacaggaacag | 79 | 169 |
| 180803 | Coding | 11 | 448 | tcttcactctccagagtcga | 55 | 170 |

TABLE 2-continued

Inhibition of mouse RANKL mRNA levels by
chimeric phosphorothioate oligonucleotides having
2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 180804 | Coding | 11 | 512 | cagttccttctgcacggccc | 44 | 171 |
| 180805 | Coding | 11 | 598 | ggcttgcctcgctgggccac | 62 | 172 |
| 180807 | Coding | 11 | 783 | agcaaatgttggcgtacagg | 74 | 173 |
| 180808 | Coding | 11 | 832 | agctgaagatagtctgtagg | 74 | 174 |
| 180809 | Coding | 11 | 867 | ggattttgatgctggtttta | 53 | 175 |
| 180810 | Coding | 11 | 925 | tcagaattgcccgaccagtt | 83 | 176 |
| 180811 | Coding | 11 | 991 | atgctaatttcttccaccagc | 67 | 177 |
| 180812 | Coding | 11 | 1024 | tccggatccagcagggaagg | 47 | 178 |
| 180813 | Stop Codon | 11 | 1092 | atgttccacgaaatgagtct | 48 | 179 |
| 180814 | 3'UTR | 11 | 1159 | gtcttacacatgtatagaca | 66 | 180 |
| 180815 | 3'UTR | 11 | 1188 | tcatacaccgtgggccatgt | 30 | 181 |
| 180816 | 3'UTR | 11 | 1278 | accgttgtgtaatcaccatg | 35 | 182 |
| 180817 | 3'UTR | 11 | 1337 | gcatcggaatacctctccca | 51 | 183 |
| 180818 | 3'UTR | 11 | 1411 | tcagtggcacatgtccaggg | 59 | 184 |
| 180819 | 3'UTR | 11 | 1507 | tgcaggtcccagcgcaatgt | 66 | 185 |
| 180820 | 3'UTR | 11 | 1513 | cttatttgcaggtcccagcg | 44 | 186 |
| 180821 | 3'UTR | 11 | 1586 | cattacacctgaaatataac | 15 | 187 |
| 180822 | 3'UTR | 11 | 1635 | aatcaaatactatagcacaa | 24 | 188 |
| 180823 | 3'UTR | 11 | 1646 | taaatattttgaatcaaata | 9 | 189 |
| 180824 | 3'UTR | 11 | 1666 | tgtcaacagtgagacatttt | 29 | 190 |
| 180825 | 3'UTR | 11 | 1687 | gtacatttaaaacattaaat | 25 | 191 |
| 180826 | 3'UTR | 11 | 1714 | tacaaagtgcaccagttaaa | 33 | 192 |
| 180827 | 3'UTR | 11 | 1738 | agctacgagtaccttcaggg | 54 | 193 |
| 180828 | 3'UTR | 11 | 1843 | tttattttgcttgcatagtt | 44 | 194 |
| 180829 | 3'UTR | 11 | 1903 | aaggcacctggtgaccaaca | 23 | 195 |
| 180830 | 3'UTR | 11 | 1906 | tgaaaggcacctggtgacca | 5 | 196 |
| 180831 | 3'UTR | 11 | 1980 | cctgacagatttcagtagcc | 54 | 197 |
| 180832 | 3'UTR | 11 | 2057 | ggaaaaaaagaaaccaaaa | 0 | 198 |
| 180833 | 3'UTR | 11 | 2156 | cagagacaatgcttttattg | 22 | 199 |

As shown in Table 2, SEQ ID NOs 155, 157, 158, 159, 160, 162, 163, 164, 166, 167, 168, 169, 170, 171, 172, 173, 174, 175, 176, 177, 178, 179, 180, 183, 184, 185, 186, 193, 194, and 197 demonstrated at least 40% inhibition of mouse RANKL expression in this experiment and are therefore preferred. More preferred are SEQ ID NOs 180 and 185. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds shown in Table 2. "Target site" indicates the first (5'-most) nucleotide number on the particular target nucleic acid to which the oligonucleotide binds. Also shown in Table 4 is the species in which each of the preferred target segments was found.

Example 17

Antisense Inhibition of Rat RANKL Expression by Chimeric Phosphorothioate Oligonucleotides Having 2'-MOE Wings and a Deoxy Gap In accordance with the present invention, a second series of antisense compounds was designed to target different regions of the rat RANKL RNA, using published sequences (GenBank accession number NM_057149.1, incorporated herein as SEQ ID NO: 18, and GenBank accession number AF425669.1, incorporated herein as SEQ ID NO: 200). The compounds are shown in Table 3. "Target site" indicates the first (5'-most) nucleotide number on the particular target nucleic acid to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on rat RANKL mRNA levels by quantitative real-time PCR as described in other examples herein. Data are averages from three experiments in which UMR-106 cells were treated with the antisense oligonucleotides of the present invention. The positive control for each datapoint is identified in the table by sequence ID number. If present, "N.D." indicates "no data".

TABLE 3

Inhibition of rat RANKL mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 180802 | Coding | 18 | 199 | gctcgaaagtacaggaacag | 40 | 169 | 1 |
| 180806 | Coding | 18 | 503 | ggcagcattgatggtgaggt | 9 | 201 | 1 |
| 180807 | Coding | 18 | 648 | agcaaatgttggcgtacagg | 48 | 173 | 1 |
| 180809 | Coding | 18 | 732 | ggattttgatgctggtttta | 57 | 175 | 1 |
| 286586 | Coding | 18 | 15 | ggtacttgccgtagtctcgg | 63 | 202 | 1 |
| 286587 | Coding | 18 | 20 | gcgcaggtacttgccgtagt | 50 | 203 | 1 |
| 286588 | Coding | 18 | 178 | gcgatgctgcagaccacctg | 63 | 204 | 1 |
| 286589 | Coding | 18 | 183 | acagagcgatgctgcagacc | 49 | 205 | 1 |
| 286590 | Coding | 18 | 188 | caggaacagagcgatgctgc | 47 | 206 | 1 |
| 286591 | Coding | 18 | 193 | aagtacaggaacagagcgat | 17 | 207 | 1 |
| 286592 | Coding | 18 | 198 | ctcgaaagtacaggaacaga | 16 | 208 | 1 |
| 286593 | Coding | 18 | 203 | ctgcgctcgaaagtacagga | 49 | 209 | 1 |
| 286594 | Coding | 18 | 208 | tccatctgcgctcgaaagta | 35 | 210 | 1 |
| 286595 | Coding | 18 | 213 | taggatccatctgcgctcga | 46 | 211 | 1 |
| 286596 | Coding | 18 | 218 | tctgttaggatccatctgcg | 58 | 212 | 1 |

TABLE 3-continued

Inhibition of rat RANKL mRNA levels by
chimeric phosphorothioate oligonucleotides having
2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 286597 | Coding | 18 | 223 | gatattctgttaggatccat | 57 | 213 | 1 |
| 286598 | Coding | 18 | 228 | cttctgatattctgttagga | 6 | 214 | 1 |
| 286599 | Coding | 18 | 238 | cgcgtgctgtcttctgatat | 46 | 215 | 1 |
| 286600 | Coding | 18 | 252 | ttctgtagaagcagcgcgtg | 13 | 216 | 1 |
| 286601 | Coding | 18 | 268 | tcacggagtctcagaattct | 63 | 217 | 1 |
| 286602 | Coding | 18 | 279 | aacctgtattttcacggagt | 48 | 218 | 1 |
| 286603 | Coding | 18 | 293 | agtcgagtcctgcaaacctg | 59 | 219 | 1 |
| 286604 | Coding | 18 | 298 | tccagagtcgagtcctgcaa | 68 | 220 | 1 |
| 286605 | Coding | 18 | 369 | tttgcacggccccttgaaag | 53 | 221 | 1 |
| 286606 | Coding | 18 | 379 | tgtaattccctttgcacggc | 37 | 222 | 1 |
| 286607 | Coding | 18 | 397 | tgtggcccacaatgtgttg | 48 | 223 | 1 |
| 286608 | Coding | 18 | 480 | caaacggctgagcctcaggc | 25 | 224 | 1 |
| 286609 | Coding | 18 | 502 | gcagcattgatggtgaggtg | 17 | 225 | 1 |
| 286610 | Coding | 18 | 529 | actttatgggaacccgatgg | 34 | 226 | 1 |
| 286611 | Coding | 18 | 542 | agaggacagactgactttat | 47 | 227 | 1 |
| 286612 | Coding | 18 | 550 | tggtaccaagaggacagact | 5 | 228 | 1 |
| 286613 | Coding | 18 | 555 | gatcatggtaccaagaggac | 39 | 229 | 1 |
| 286614 | Coding | 18 | 571 | atcttggcccagcctcgatc | 41 | 230 | 1 |
| 286615 | Coding | 18 | 576 | tagagatcttggcccagcct | 45 | 231 | 1 |
| 286616 | Coding | 18 | 581 | catgttagagatcttggccc | 31 | 232 | 1 |
| 286617 | Coding | 18 | 601 | agttttccgttgcttaacgt | 52 | 233 | 1 |
| 286618 | Coding | 18 | 607 | acccttagttttccgttgct | 57 | 234 | 1 |
| 286619 | Coding | 18 | 612 | ggttaacccttagttttccg | 61 | 235 | 1 |
| 286620 | Coding | 18 | 617 | atcttggttaacccttagtt | 48 | 236 | 1 |
| 286621 | Coding | 18 | 622 | aagccatcttggttaaccct | 33 | 237 | 1 |
| 286622 | Coding | 18 | 627 | aatagaagccatcttggtta | 12 | 238 | 1 |
| 286623 | Coding | 18 | 628 | taatagaagccatcttggtt | 16 | 239 | 1 |
| 286624 | Coding | 18 | 632 | caggtaatagaagccatctt | 22 | 240 | 1 |
| 286625 | Coding | 18 | 637 | gcgtacaggtaatagaagcc | 50 | 241 | 1 |
| 286626 | Coding | 18 | 642 | tgttggcgtacaggtaatag | 41 | 242 | 1 |
| 286627 | Coding | 18 | 647 | gcaaatgttggcgtacaggt | 53 | 243 | 1 |
| 286628 | Coding | 18 | 691 | agatagtccgcaggtacgct | 24 | 244 | 1 |
| 286629 | Coding | 18 | 703 | accatcagctgaagatagtc | 63 | 245 | 1 |
| 286630 | Coding | 18 | 717 | ttttaacgacatataccatc | 44 | 246 | 1 |

TABLE 3-continued

Inhibition of rat RANKL mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 286631 | Coding | 18 | 724 | atgctggttttaacgacata | 35 | 247 | 1 |
| 286632 | Coding | 18 | 736 | cttgggattttgatgctggt | 51 | 248 | 1 |
| 286633 | Coding | 18 | 776 | ccagttcttagtgctccccc | 4 | 249 | 1 |
| 286634 | Coding | 18 | 793 | aattcagaattccctgacca | 21 | 250 | 1 |
| 286635 | Coding | 18 | 802 | taaaagtggaattcagaatt | 11 | 251 | 1 |
| 286636 | Coding | 18 | 807 | tggaataaaagtggaattca | 21 | 252 | 1 |
| 286637 | Coding | 18 | 899 | cgcatcttgatccggatcca | 27 | 253 | 1 |
| 286638 | Coding | 18 | 906 | agtacgtcgcatcttgatcc | 26 | 254 | 1 |
| 286639 | Coding | 18 | 911 | cccaaagtacgtcgcatctt | 48 | 255 | 1 |
| 286640 | Coding | 18 | 916 | aaagccccaaagtacgtcgc | 56 | 256 | 1 |
| 286641 | Coding | 18 | 921 | ctttgaaagccccaaagtac | 49 | 257 | 1 |
| 286642 | Stop Codon | 18 | 938 | tcagtctatgtcttgaactt | 41 | 258 | 1 |
| 286643 | 3'UTR | 200 | 178 | gcatatccatgctaaggctc | 69 | 259 | 1 |
| 286644 | 3'UTR | 200 | 231 | gtcttacacatgtatctaca | 57 | 260 | 1 |
| 286645 | 3'UTR | 200 | 238 | cttagtagtcttacacatgt | 51 | 261 | 1 |
| 286646 | 3'UTR | 200 | 262 | ttttgtacaacgtgggccac | 53 | 262 | 1 |
| 286647 | 3'UTR | 200 | 293 | gacctgtacagggtcgagag | 53 | 263 | 1 |
| 286648 | 3'UTR | 200 | 346 | ccattgtgtgatcaccatga | 72 | 264 | 1 |
| 286649 | 3'UTR | 200 | 463 | tagacccagagactatgtat | 25 | 265 | 1 |
| 286650 | 3'UTR | 200 | 482 | gtggcacaggcccaggagtt | 53 | 266 | 1 |
| 286651 | 3'UTR | 200 | 491 | aggttctcagtggcacaggc | 80 | 267 | 1 |
| 286652 | 3'UTR | 200 | 523 | ctctgcaatgtaacggtacc | 53 | 268 | 1 |
| 286653 | 3'UTR | 200 | 535 | aaaccatcatttctctgcaa | 58 | 269 | 1 |
| 286654 | 3'UTR | 200 | 588 | acttatttgcaggttccagc | 55 | 270 | 1 |
| 286655 | 3'UTR | 200 | 666 | gaaaaccttacacctgaaat | 0 | 271 | 1 |
| 286656 | 3'UTR | 200 | 675 | ttttgcacagaaaaccttac | 12 | 272 | 1 |
| 286657 | 3'UTR | 200 | 778 | ccagttaaatacatcttgac | 10 | 273 | 1 |

As shown in Table 3, SEQ ID NOs 169, 173, 175, 202, 203, 204, 205, 206, 209, 211, 212, 213, 215, 217, 218, 219, 220, 221, 223, 227, 230, 231, 233, 234, 235, 236, 241, 242, 243, 245, 246, 248, 255, 256, 257, 258, 259, 260, 261, 262, 263, 264, 266, 267, 268, 269, and 270 demonstrated at least 40% inhibition of rat RANKL expression in this experiment and are therefore preferred. More preferred are SEQ ID NOs 259, 264, and 267. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds shown in Tables 2 and 3. "Target site" indicates the first (5'-most) nucleotide number on the particular target nucleic acid to which the oligonucleotide binds. Also shown in Table 4 is the species in which each of the preferred target segments was found.

TABLE 4

Sequence and position of preferred target segments identified in RANKL.

| SITE ID | TARGET SEQ ID NO | TARGET SITE | SEQUENCE | REV COMP OF SEQ ID | ACTIVE IN | SEQ ID NO |
|---|---|---|---|---|---|---|
| 95966 | 11 | 20 | ctgccaggacctttgtgaac | 155 | M. musculus | 274 |
| 95968 | 11 | 52 | gggccgtggcggagtctgct | 157 | M. musculus | 275 |
| 95969 | 11 | 58 | tggcggagtctgctcggcgg | 158 | M. musculus | 276 |
| 95970 | 11 | 95 | gagagaacgatcgcggagca | 159 | M. musculus | 277 |
| 95971 | 11 | 99 | gaacgatcgcggagcagggc | 160 | M. musculus | 278 |
| 95973 | 11 | 137 | gcgccatgcgccgggccagc | 162 | M. musculus | 279 |
| 95974 | 11 | 140 | ccatgcgccgggccagccga | 163 | M. musculus | 280 |
| 95975 | 11 | 142 | atgcgccgggccagccgaga | 164 | M. musculus | 281 |
| 95977 | 11 | 262 | ccgccacccgccgcctcccg | 166 | M. musculus | 282 |
| 95978 | 11 | 270 | cgccgcctcccgctccatgt | 167 | M. musculus | 283 |
| 95979 | 11 | 271 | gccgcctcccgctccatgtt | 168 | M. musculus | 284 |
| 95980 | 11 | 340 | ctgttcctgtactttcgagc | 169 | M. musculus | 285 |
| 95981 | 11 | 448 | tcgactctggagagtgaaga | 170 | M. musculus | 286 |
| 95982 | 11 | 512 | gggccgtgcagaaggaactg | 171 | M. musculus | 287 |
| 95983 | 11 | 598 | gtggcccagcgaggcaagcc | 172 | M. musculus | 288 |
| 95985 | 11 | 783 | cctgtacgccaacatttgct | 173 | M. musculus | 289 |
| 95986 | 11 | 832 | cctacagactatcttcagct | 174 | M. musculus | 290 |
| 95987 | 11 | 867 | taaaaccagcatcaaaatcc | 175 | M. musculus | 291 |
| 95988 | 11 | 925 | aactggtcgggcaattctga | 176 | M. musculus | 292 |
| 95989 | 11 | 991 | gctggtgaagaaattagcat | 177 | M. musculus | 293 |
| 95990 | 11 | 1024 | ccttccctgctggatccgga | 178 | M. musculus | 294 |
| 95991 | 11 | 1092 | agactcatttcgtggaacat | 179 | M. musculus | 295 |
| 95992 | 11 | 1159 | tgtctatacatgtgtaagac | 180 | M. musculus | 296 |
| 95995 | 11 | 1337 | tgggagaggtattccgatgc | 183 | M. musculus | 297 |
| 95996 | 11 | 1411 | ccctggacatgtgccactga | 184 | M. musculus | 298 |
| 95997 | 11 | 1507 | acattgcgctgggacctgca | 185 | M. musculus | 299 |
| 95998 | 11 | 1513 | cgctgggacctgcaaataag | 186 | M. musculus | 300 |
| 96005 | 11 | 1738 | ccctgaaggtactcgtagct | 193 | M. musculus | 301 |
| 96006 | 11 | 1843 | aactatgcaagcaaaataaa | 194 | M. musculus | 302 |
| 96009 | 11 | 1980 | ggctactgaaatctgtcagg | 197 | M. musculus | 303 |
| 202604 | 18 | 15 | ccgagactacggcaagtacc | 202 | R. norvegicus | 304 |
| 202605 | 18 | 20 | actacggcaagtacctgcgc | 203 | R. norvegicus | 305 |
| 202606 | 18 | 178 | caggtggtctgcagcatcgc | 204 | R. norvegicus | 306 |
| 202607 | 18 | 183 | ggtctgcagcatcgctctgt | 205 | R. norvegicus | 307 |
| 202608 | 18 | 188 | gcagcatcgctctgttcctg | 206 | R. norvegicus | 308 |

TABLE 4-continued

Sequence and position of preferred target segments identified in RANKL.

| SITE ID | TARGET SEQ ID NO | TARGET SITE | SEQUENCE | REV COMP OF SEQ ID | ACTIVE IN | SEQ ID NO |
|---|---|---|---|---|---|---|
| 202611 | 18 | 203 | tcctgtactttcgagcgcag | 209 | R. norvegicus | 309 |
| 202613 | 18 | 213 | tcgagcgcagatggatccta | 211 | R. norvegicus | 310 |
| 202614 | 18 | 218 | cgcagatggatcctaacaga | 212 | R. norvegicus | 311 |
| 202615 | 18 | 223 | atggatcctaacagaatatc | 213 | R. norvegicus | 312 |
| 202617 | 18 | 238 | atatcagaagacagcacgcg | 215 | R. norvegicus | 313 |
| 202619 | 18 | 268 | agaattctgagactccgtga | 217 | R. norvegicus | 314 |
| 202620 | 18 | 279 | actccgtgaaaatacaggtt | 218 | R. norvegicus | 315 |
| 202621 | 18 | 293 | caggtttgcaggactcgact | 219 | R. norvegicus | 316 |
| 202622 | 18 | 298 | ttgcaggactcgactctgga | 220 | R. norvegicus | 317 |
| 202623 | 18 | 369 | ctttcaaggggccgtgcaaa | 221 | R. norvegicus | 318 |
| 202625 | 18 | 397 | caacacattgtggggccaca | 223 | R. norvegicus | 319 |
| 202629 | 18 | 542 | ataaagtcagtctgtcctct | 227 | R. norvegicus | 320 |
| 202632 | 18 | 571 | gatcgaggctgggccaagat | 230 | R. norvegicus | 321 |
| 202633 | 18 | 576 | aggctgggccaagatctcta | 231 | R. norvegicus | 322 |
| 202635 | 18 | 601 | acgttaagcaacggaaaact | 233 | R. norvegicus | 323 |
| 202636 | 18 | 607 | agcaacggaaaactaagggt | 234 | R. norvegicus | 324 |
| 202637 | 18 | 612 | cggaaaactaagggttaacc | 235 | R. norvegicus | 325 |
| 202638 | 18 | 617 | aactaagggttaaccaagat | 236 | R. norvegicus | 326 |
| 202643 | 18 | 637 | ggcttctattacctgtacgc | 241 | R. norvegicus | 327 |
| 202644 | 18 | 642 | ctattacctgtacgccaaca | 242 | R. norvegicus | 328 |
| 202645 | 18 | 647 | acctgtacgccaacatttgc | 243 | R. norvegicus | 329 |
| 202647 | 18 | 703 | gactatcttcagctgatggt | 245 | R. norvegicus | 330 |
| 202648 | 18 | 717 | gatggtatatgtcgttaaaa | 246 | R. norvegicus | 331 |
| 202650 | 18 | 736 | accagcatcaaaatcccaag | 248 | R. norvegicus | 332 |
| 202657 | 18 | 911 | aagatgcgacgtactttggg | 255 | R. norvegicus | 333 |
| 202658 | 18 | 916 | gcgacgtactttggggcttt | 256 | R. norvegicus | 334 |
| 202659 | 18 | 921 | gtactttggggcttcaaag | 257 | R. norvegicus | 335 |
| 202660 | 18 | 938 | aagttcaagacatagactga | 258 | R. norvegicus | 336 |
| 202661 | 200 | 178 | gagccttagcatggatatgc | 259 | R. norvegicus | 337 |
| 202662 | 200 | 231 | tgtagatacatgtgtaagac | 260 | R. norvegicus | 338 |
| 202663 | 200 | 238 | acatgtgtaagactactaag | 261 | R. norvegicus | 339 |
| 202664 | 200 | 262 | gtggcccacgttgtacaaaa | 262 | R. norvegicus | 340 |
| 202665 | 200 | 293 | ctctcgaccctgtacaggtc | 263 | R. norvegicus | 341 |
| 202666 | 200 | 346 | tcatggtgatcacacaatgg | 264 | R. norvegicus | 342 |
| 202668 | 200 | 482 | aactcctgggcctgtgccac | 266 | R. norvegicus | 343 |
| 202669 | 200 | 491 | gcctgtgccactgagaacct | 267 | R. norvegicus | 344 |

TABLE 4-continued

Sequence and position of preferred target segments identified in RANKL.

| SITE ID | TARGET SEQ ID NO | TARGET SITE | SEQUENCE | REV COMP OF SEQ ID | ACTIVE IN | SEQ ID NO |
|---|---|---|---|---|---|---|
| 202670 | 200 | 523 | ggtaccgttacattgcagag | 268 | R. norvegicus | 345 |
| 202671 | 200 | 535 | ttgcagagaaatgatggttt | 269 | R. norvegicus | 346 |
| 202672 | 200 | 588 | gctggaacctgcaaataagt | 270 | R. norvegicus | 347 |
| 95980 | 18 | 199 | ctgttcctgtactttcgagc | 169 | R. norvegicus | 285 |
| 95985 | 18 | 648 | cctgtacgccaacatttgct | 173 | R. norvegicus | 289 |
| 95987 | 18 | 732 | taaaaccagcatcaaaatcc | 175 | R. norvegicus | 291 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of RANKL.

According to the present invention, antisense compounds include antisense oligomeric compounds, antisense oligonucleotides, ribozymes, external guide sequence (EGS) oligonucleotides, alternate splicers, primers, probes, and other short oligomeric compounds that hybridize to at least a portion of the target nucleic acid.

Example 18

Western Blot Analysis of RANKL Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to RANKL is used, with a radiolabeled or fluorescently labeled secondary antibody directed against the primary antibody species. Bands are visualized using a PHOSPHORIMAGER™ (Molecular Dynamics, Sunnyvale Calif.).

Example 19

Antisense Inhibition of Mouse RANKL Expression by Chimeric Phosphorothioate Oligonucleotides Having 2'-MOE Wings and a Deoxy Gap: Dose Response In accordance with the present invention, a subset of the antisense oligonucleotides in Example 16 was further investigated in dose-response studies. The oligonucleotides used in this investigation were ISIS 180812 (SEQ ID NO: 178), ISIS 180814 (SEQ ID NO: 180), ISIS 180819 (SEQ ID NO: 185), ISIS 180828 (SEQ ID NO: 194) and the control oligonucleotide ISIS 101757 (AGGTGCTCAGGACTCCATTT, SEQ ID NO: 355). ISIS 101757 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

C2C12 cells were treated with the oligonucleotides at 10, 50, 75, 100, and 150 nM as described in other examples herein. The compounds were analyzed for their effect on mouse RANKL mRNA levels in C2C12 cells by quantitative real-time PCR as described in other examples herein. The results are expressed as percent inhibition relative to the untreated control. The data, shown in Table 5, are averages from two experiments and illustrate the oligonucleotides of the present invention are able to downregulate RANKL mRNA expression in a dose-dependent manner.

TABLE 5

Inhibition of mouse RANKL mRNA levels by chimeric phosphorothioate oligonucleotides having 2'-MOE wings and a deoxy gap

| | ISIS # | | | | |
|---|---|---|---|---|---|
| | 180812 | 180814 | 180819 | 180828 | 101757 |
| Dose (nM) | % Inhibition of RANKL mRNA | | | | |
| 10 | 0 | 12 | 41 | 31 | N.D. |
| 50 | 5 | 14 | 39 | 43 | 17 |
| 75 | 13 | 61 | 57 | 23 | N.D. |
| 100 | 20 | 70 | 71 | 31 | 13 |
| 150 | 45 | 81 | 75 | 40 | N.D. |

Example 20

Short-Term Bone Resorption Model: RANKL mRNA Expression and Serum Calcium Levels After PTH Infusion Parathyroidectomized rats are a well-established, short-term model of bone resorption and are useful in the investigation of antiresorptive agents. However, it is difficult to surgically remove only the parathyroid gland of rodents, and the inadvertent removal of the adjacent thyroid gland often has effects on thyroid hormone levels that introduce into the experiment an undesirable level of variability. Continuous infusion of parathyroid hormone (PTH) into intact, young (6-9 weeks old) mice reproduces the short-term bone resorption activity observed in parathyroidectomized rodents and is thus a useful model for the study of antiresorptive agents. The PTH infusion activates bone osteoclasts and causes them to degrade bone matrix, with a resulting rise in serum calcium.

In accordance with the present invention, serum calcium concentration and RANKL mRNA expression were evaluated in a short-term mouse model of bone resorption. Female, Swiss-Webster mice (5-8 weeks old) were placed on a low calcium diet and implanted with mini-pumps delivering PTH continuously. The pumps were calibrated to deliver 1 ug PTH per 100 g bodyweight per 6 hour time period (1 ug/100 g/6 hr). With this procedure, over a 24 hour period, a total of 4 ug PTH per 100 g body weight is delivered (4 ug/100 g/24 hr). PTH infusion was conducted in these mice for 6, 12, 18 and 24 hours. At the end of each time period, the mice were sacrificed and measurements were made of the serum calcium, using the Sigma Diagnostics Calcium Kit (Sigma-Aldrich), and RANKL mRNA expression in the proximal tibia, as described in other examples herein. The data are expressed as percent increase relative to mice that received no PTH treatment. The results, shown in Table 6, are the average of three mice per time point and demonstrate that PTH infusion increases serum calcium concentration as much as 230% after 24 hours. The data also demonstrate that a large increase in RANKL mRNA expression in proximal tibia is seen after 6 hours of PTH infusion.

TABLE 6

Serum calcium concentration and RANKL mRNA in mice infused with 4 ug/100 g PTH over 24 hours

| Time Hours | Serum Calcium Concentration % control | RANKL mRNA % control |
|---|---|---|
| 0 | 100 | 100 |
| 6 | 109 | 787 |
| 12 | 115 | 242 |
| 18 | 125 | 117 |
| 24 | 230 | 205 |

Example 21

RANKL mRNA Expression in Primary Mouse Osteoblast Cells After PTH Treatment: Time Course Study In a further embodiment of this invention, the effect of PTH treatment on the expression of RANKL was determined in primary osteoblast cells isolated from mice skull caps. Primary osteoblastic cells were treated for 24 hours with either saline or the transfection reagent FuGENE 6 (Roche Applied Science, Indianapolis, Ind.). During the last 2 hours, the cells were treated with 10 nM PTH. The RNA was then harvested and the expression levels of RANKL mRNA were measured by the methods described herein. The results are expressed as percent increase over untreated cells. The data are summarized in Table 7 and demonstrate that, in the presence of either saline or FuGENE 6, RANKL mRNA is unregulated in response to PTH, with peak expression occurring after two hours of PTH treatment.

TABLE 7

Effect of PTH treatment on RANKL mRNA expression in primary osteoblast cells in the presence of saline or FuGENE 6

| | RANKL mRNA % control | |
|---|---|---|
| Time (hours) | Saline Treatment | FuGENE 6 Treatment |
| 0 | 100 | 100 |
| 0.5 | 168 | 185 |
| 1 | 700 | 750 |
| 2 | 908 | 1275 |
| 4 | 383 | 467 |
| 6 | 326 | 340 |

Example 22

Antisense Inhibition RANKL mRNA After PTH Treatment in Primary Osteoblast Cells: Dose Response Study In a further embodiment of this invention, the effect of RANKL antisense oligonucleotides and PTH treatment on the expression of RANKL was determined in primary osteoblast cells isolated from mice skull caps.

ISIS 143624 (TGCTCAGCGAGTGTGCCAGC, SEQ ID NO: 348) was used as a control oligonucleotide. ISIS 143624 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

Primary osteoblast cells were transfected for 24 hours with either Isis 180819 (SEQ ID NO: 185) or the control oligo ISIS 143624 (SEQ ID NO: 348) at a dose of 63 mM, 125 nM, 250 nM, or 500 nM by the methods described herein but using the transfection reagent FuGENE 6 (Roche Applied Science, Indianapolis, Ind.). During the last 2 hours of oligonucleotide transfection, the cells were treated with 10 nM PTH. The RNA was then harvested and the expression levels of RANK mRNA were measured by the methods described herein. The results are expressed as percent inhibition relative to PTH treatment alone and represent the average from three experiments. The data are summarized in Table 8 and illustrate that the oligonucleotide of the present invention is able to inhibit the PTH-induced increase in RANKL mRNA expression, which was demonstrated in Example 21, in a dose dependent manner. The control oligonucleotide is unable to reduce RANKL mRNA levels.

TABLE 8

Antisense inhibition RANKL mRNA after PTH treatment in primary osteoblast cells: dose response study

| | % RANKL mRNA inhibition | |
|---|---|---|
| PTH alone | 0 | |
| Dose of oligonucleotide | ISIS # | |
| | 180819 | 143624 |
| 63 nM | 19 | 4 |
| 125 nM | 39 | 3 |

TABLE 8-continued

Antisense inhibition RANKL mRNA after PTH treatment
in primary osteoblast cells: dose response study

| | | |
|---|---|---|
| 250 nM | 71 | 0 |
| 500 nM | 85 | 9 |

Example 23

Effects of Antisense Inhibition of RANKL After PTH Infusion in the Proximal Tibia and Calvaria in Mice: Dose Response In accordance with the present invention, the levels of RANKL in the proximal tibia and calvaria in mice were measured following antisense oligonucleotide treatment and PTH infusion.

Female Swiss-Webster mice (5-8 wks old) fed a low-calcium diet were treated with ISIS 180819 (SEQ ID NO: 185) by subcutaneous injection at a dose of either 30 mg/kg or 50 mg/kg or intraperitoneal injection at a dose of either 15 mg/kg, 30 mg/kg or 50 mg/kg. After 2 weeks of daily treatment, the mice were infused with PTH at a dose of 1 ug/100 g/6 hr. After 24 hours of PTH infusion (total PTH delivery of 4 ug/100 g), the mice were sacrificed. The proximal tibia and calvaria were isolated and the level of RANKL mRNA expression was determined in each using two different primer-probe sets to confirm the results. The first primer-probe set was #1207, consisting of TTTATTCCATAAATGT-TGGGGGATT (forward primer, SEQ ID NO: 349), TTGGA-CACCTGAATGCTAATTT (reverse primer, SEQ ID NO: 350) and TTCAAGCTCCGAGCTGGTGAAGA (probe, SEQ ID NO: 351). The second primer-probe set was #1015, consisting of CAACCCTTCCCTGCTGGA (forward primer, SEQ ID NO: 352), CAGTCTATGTCCT-GAACTTTGAAAGC (reverse primer, SEQ ID NO: 353) and CCGGATCAAGATGCGACGTACTTTGG (probe, SEQ ID NO: 354). The results are expressed as percent inhibition relative to PTH treatment alone and represent the average of eight mice per group. The data are summarized in Table 9 and show that treatment of mice with the oligonucleotide of the present invention is capable of inhibiting the PTH-induced increase in RANKL mRNA expression in the proximal tibia and calvaria in a dose-dependent manner, with greater inhibition occurring in the calvaria.

TABLE 9

Effect antisense inhibition of RANKL mRNA levels in
the proximal tibia and calvaria of mice following
PTH treatment: dose response and delivery method

| | % Inhibition of RANKL | | | |
|---|---|---|---|---|
| | Proximal tibia Primer-Probe set | | Calvaria Primer-Probe set | |
| Oligonucleotide | | | | |
| Dose (mg/kg) | 1207 | 1015 | 1207 | 1015 |
| PTH alone | 0 | 0 | 0 | 0 |
| Subcutaneous injection | | | | |
| 30 | 10 | 5 | 38 | 38 |
| 50 | 36 | 32 | 52 | 60 |
| Intraperitoneal injection | | | | |
| 15 | 0 | 2 | N.D. | N.D. |
| 30 | 0 | 0 | 24 | 39 |
| 50 | 13 | 21 | 54 | 51 |

Example 24

Serum Calcium Concentration 24 Hours After PTH Infusion in Mice Treated with RANKL Antisense Oligonucleotides: Dose Response In accordance with the present invention, the effect of antisense oligonucleotide inhibition on PTH-induced serum calcium concentration increase was measured in mice. The serum calcium concentration in mice was measured as a function of dosing schedule.

Female Swiss-Webster (5-8 wks old) mice fed a low-calcium diet were dosed subcutaneously for two weeks with either the oligonucleotides ISIS 180819 (SEQ ID NO: 185) or 180814 (SEQ ID NO: 180) at concentrations of 5 mg/kg, 15 mg/kg, 30 mg/kg, or 40 mg/kg. A control group of mice were treated with calcitonin (400 ng) plus PTH (1 ug/100 g/6 hr), PTH (1 ug/100 g/6 hr) alone or saline. Treatment with oligonucleotides was followed with infusion of PTH by subcutaneously implanted mini-pumps at a dose of 1 ug/100 g/6 hr. After 24 hours of PTH infusion (total PTH delivery of 4 ug/100 g), the mice were sacrificed and the serum calcium concentration was measured with the Sigma Diagnostics Calcium Kit (Sigma-Aldrich). The data are averages from eight mice and are summarized in Table 10. The data illustrate that the oligonucleotides of the present invention can, in a dose-dependent manner, lower serum calcium concentration following PTH infusion.

TABLE 10

Serum calcium concentration 24 hours after PTH
infusion in mice treated with RANKL antisense oligonucleotides
for two weeks: dose response

| | ISIS 180819 | | ISIS 180814 | |
|---|---|---|---|---|
| | Serum Calcium, mg/dl | RANKL mRNA, % inhib | Serum Calcium, mg/dl | RANKL mRNA, % inhib |
| No oligonucleotide treatment | | | | |
| Saline | 10 | 58 | 10 | 53 |
| PTH + calcitonin | 14 | 0 | 13 | 0 |
| PTH | 22 | 0 | 22 | 0 |
| Isis oligonucleotide-treated | | | | |
| 5 mg/kg | 21 | 0 | 22 | 0 |
| 15 mg/kg | 17 | 0 | 20 | 0 |
| 30 mg/kg | 19 | 0 | 18 | 27 |
| 40 mg/kg | N.D. | N.D. | 19 | 6 |

As illustrated in this and other examples herein, the inhibition of PTH-induced serum calcium concentration by RANKL antisense oligonucleotides (35% inhibition, n=8) is effective, although less so than inhibition by calcitonin, a known antiresorptive agent (66% inhibition, n=8). If desired, additional antisense oligonucleotides can be screened in a like manner to identify those with more or less inhibitory properties.

Example 25

Modulation of Bone Resorption in Mouse Model of Hypercalcemia of Malignancy

Solid tumors such as small cell carcinoma of the lung and renal cell carcinomas are frequently associated with a paraneoplastic syndrome that includes severe and often life-threatening hypercalcemia, known as humoral hypercalcemia of malignancy. This condition is attributable to markedly enhanced osteoclast-mediated bone degradation, which results in elevated serum calcium levels (Oyajobi et al., 2001, Cancer Res., 61, 2572-2578). A secreted form of RANKL is expressed by cancer cells responsible for humoral hypercalcemia of malignancy (Nagai et al., Biochem. Biophys. Res. Commun., 2000, 269, 532-536). Accordingly, in a further embodiment of the present invention, RANKL antisense oligonucleotides are tested for their potential to prevent the development of or to ameliorate humoral hypercalcemia of malignancy.

Hypercalcemia is induced by injecting tumorigenic cells into immunocomprimised mice, 22 days after which fullblown hypercalcemia is observed (Oyajobi et al., 2001, Cancer Res., 61, 2572-2578).

Female 4 to 6 week old Balb/c athymic nude mice are inoculated with a carcinoma cell line, such as a lung small cell carcinoma cell line, in the subcutaneous tissue of the flank. A total of 1×106 cells, in 200 ul of phosphate-buffered saline, is injected. Control animals receive an injection of saline alone. Saline- and tumorigenic cell-injected animals are divided into two groups. The first group receives a subcutaneous injection of RANKL antisense oligonucleotide the same day as tumorigenic cell injection, to investigate the capacity of the antisense compounds to prevent hypercalcemia. Injections in the first group are administered subcutaneously, twice per week for 3 weeks. The second group receives a subcutaneous injection of RANKL antisense oligonucleotide 3 weeks after tumor inoculation, to investigate the ability of RANKL antisense compounds to ameliorate existing hypercalcemia. Injections in the second group are administered subcutaneously twice per week for an additional 2 weeks after the onset of full-blown hypercalcemia. Animals are injected with RANKL antisense oligonucleotides or control oligonucleotide at a dose of 15 or 30 mg/kg.

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the end of the treatment period, the mice are evaluated for osteoclast-mediated bone resorption. To determine whether RANKL antisense oligonucleotides can block osteoclast formation in the CIA model, osteoclast number in the femoral and tibial bones is determined. Femora and tibia are removed, fixed in 4% formalin, decalcified in EDTA and embedded in paraffin. Sections are cut and stained for the presence of TRAP, a marker of differentiated osteoclasts. Bone sections are also stained with hematoxylin and eosin to visualize nuclei and cytoplasm. Sections are evaluated for bone integrity and histomorphometric analysis is performed to compare bone volume to total volume. RANKL mRNA levels in the proximal tibia, calvaria and bone marrow of treated mice is measured by real-time PCR.

Example 26

Modulation of Bone Resorption in a Mouse Model of Multiple Myeloma

Multiple myeloma is a cancer in which osteoporosis and bone destruction are prominent features. Myeloma cell lines stimulate RANKL expression while inhibiting OPG expression by bone marrow stromal cells, resulting in a disruption of the balance between RANKL and OPG levels, followed by the aberrant production and activation of osteoclasts, which leads to bone destruction (Pearse et al., Proc. Natl. Acad. Sci. USA, 2001, 98, 11581-11586). Accordingly, the antisense oligonucleotides of the present invention are evaluated as potential inhibitors of bone destruction in a mouse model of multiple myeloma.

Aging mice of the inbred strain C57Bl/KalwRij develop monoclonal proliferative B-cell disorders with a high frequency, and in a few cases, develop multiple myeloma. These spontaneous multiple myelomas are called the 5TMM series and are extensively characterized, particularly the 5T2MM line, which represents a model situation of the most common forms of human multiple myeloma (Asosingh et al., Hematol. J., 2000, 1, 351-356.

The 5T2MM model is generated by propagating the bone marrow of diseased mice in young recipient mice. Multiple myeloma cells isolated and purified from the bone marrow of the long bones of aging male C57Bl/KalwRij 5T2MM-bearing mice are injected in the lateral tail vein of young recipients.

The recipient animals are divided into three groups. One group receives a subcutaneous saline injection, the second receives a subcutaneous injection of a control oligonucleotide and the third receives a subcutaneous injection of 30 or 50 mg/kg RANKL antisense oligonucleotide. Injections are administered twice per week for four weeks. Tumor progression is monitored by serum paraprotein quantification using ELISA or electrophoresis.

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the end of the 4 week treatment period, the mice are sacrificed, bone marrow is isolated from the hind legs, and the proportion of tumor cells is determined by staining the cells with an anti-5T2MM idiotype antibody and analysis by flow cytometry.

To determine whether RANKL antisense oligonucleotides can block osteoclast formation in the 5T2MM model, osteoclast number in the femoral bone is determined. Femora are removed, fixed in 4% formalin, decalcified in EDTA and embedded in paraffin. Sections are cut and stained for the presence of TRAP, a marker of differentiated osteoclasts. Bone sections are also stained with hematoxylin and eosin to visualize nuclei and cytoplasm. Sections are evaluated for bone integrity and histomorphometric analysis is performed to compare bone volume to total volume. RANKL mRNA levels in the proximal tibia, calvaria and bone marrow of treated mice is measured by real-time PCR.

Example 27

Modulation of Bone Resorption in a Mouse Model of Breast Cancer-Related Osteolysis Breast carcinoma is the most common tumor type associated with osteolytic lesions that result from bone metastases. Osteolysis results in the complications of bone pain, fracture, hypercalcemia and nerve-compression syndromes. Histologic and scanning electron microscopic analysis of osteolytic bone metastases indicate that bone destruction is mediated by osteoclasts. Consequently, the compounds of the present invention are evaluated in a mouse model of breast carcinoma, to evaluate their potential to prevent or ameliorate osteolytic lesions that result from bone metastases (Guise, Cancer, 2000, 88, 2892-2898).

A mouse model of bone metastasis in breast carcinoma is generated by the injection of breast carcinoma cells into immunocompromised (nude) mice. Four to five weeks after the inoculation of MDA-231 cells, metastases are selectively developed in bone. Histologic examination demonstrates that bone marrow cavity is replaced by metastatic breast carcinoma cells with increased numbers of osteoclasts.

One to five hundred thousand human cancer cells, such as MDA-MB-231 human estrogen-independent breast carcinoma cells (obtained from American Type Culture Collection, Manassas, Va.), are inoculated into the left ventricle of the heart in 4 to 6-week-old female nude mice. The recipient animals are divided into two groups. One group receives treatment at the time of cancer cell inoculation, and the second receives treatment after bone metastases have been established (as determined by radiograph). Each of these treatment groups is further subdivided into three groups; the first receives a saline injection, the second receives a subcutaneous injection of 30 or 50 mg/kg control oligonucleotide and the third receives a subcutaneous injection of 30 or 50 mg/kg RANKL antisense oligonucleotide. Injections are administered twice per week for four weeks.

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the end of the 4 week treatment period, the mice are sacrificed, bone marrow is isolated from the hind legs, fixed in 4% formalin, embedded in paraffin, sectioned and the extent of tumor colonization is determined by routine histological staining of paraffin-embedded bone sections stained with hematoxylin and eosin, to visualize nuclei and cytoplasm. Histomorphometric analysis of bone sections is also performed to compare bone volume to total volume. To determine whether RANKL antisense oligonucleotides can block osteoclast formation in the bone metastasis of breast carcinoma model, osteoclast number in the femoral bone is determined. Femora are removed, fixed in 4% formalin, decalcified in EDTA and embedded in paraffin. Sections are cut and stained for the presence of TRAP, a marker of differentiated osteoclasts. RANKL mRNA levels in the proximal tibia, calvaria and bone marrow of treated mice is measured by real-time PCR.

Example 28

Modulation of Bone Resorption in Mouse Model of Collagen-Induced Arthritis

Rheumatoid arthritis is a chronic inflammatory disease characterized by progressive osteoclast-mediated bone resorption. Rheumatoid arthritis synovial fluid contains osteoclast precursors, RANKL-expressing T-cells and OPG-producing B-cells. Cultured macrophages from rheumatoid arthritis synovial fluid can differentiate into osteoclasts in a RANKL-dependent process (Itonaga et al., J. Pathol., 2000, 192, 97-104).

Collagen-induced arthritis (CIA) is used as a mouse model for rheumatoid arthritis (Durie, A., et al., Clin. Immunol. Immunopathol., 1994, 17, 11-18). In accordance with the present invention, the mouse model of collagen-induced arthritis is used to assess antisense RANKL compounds for their ability to prevent bone resorption accompanying this condition.

Female DBA/1LacJ mice (Jackson Laboratories, Bar Harbor, Me.) between the ages of 6 and 8 weeks are immunized (day 0) at the base of the tail with 100 µg of bovine type II collagen which is emulsified in Complete Freund's Adjuvant (CFA). On day 7, a second booster dose of collagen is administered by the same route. On day 14, the mice are injected subcutaneously with 100 µg of lipopolysaccharide (LPS). Oligonucleotide is administered intraperitoneally daily (10 mg/kg bolus) starting on day −3 (three days before day 0) and continuing for the duration of the study. Control animals receive injection of saline or a control oligonucleotide.

Weights are recorded weekly. Mice are inspected daily for the onset of CIA. Paw widths are rear ankle widths of affected and unaffected joints are measured three times a week using a constant tension caliper. Limbs are clinically evaluated and graded on a scale from 0-4 (with 4 being the highest).

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the end of the treatment period, the mice are evaluated for osteoclast-mediated bone resorption. To determine whether RANKL antisense oligonucleotides can block osteoclast formation in the CIA model, osteoclast number in the femoral and tibial bones is determined. Femora and tibia are removed, fixed in 4% formalin, decalcified in EDTA and embedded in paraffin. Sections are cut and stained for the presence of TRAP, a marker of differentiated osteoclasts. Bone sections are also stained with hematoxylin and eosin to visualize nuclei and cytoplasm. Sections are evaluated for bone integrity and histomorphometric analysis is performed to compare bone volume to total volume. RANKL mRNA levels in the proximal tibia, calvaria and bone marrow of treated mice is measured by real-time PCR.

Example 29

Modulation of Bone Resorption in a Rat Model of Adjuvant-Induced Arthritis

Rheumatoid arthritis is a chronic inflammatory disease characterized by progressive osteoclast-mediated bone resorption. Rheumatoid arthritis synovial fluid contains osteoclast precursors, RANKL-expressing T-cells and OPG-producing B-cells. Cultured macrophages from rheumatoid arthritis synovial fluid can differentiate into osteoclasts in a RANKL-dependent process (Itonaga et al., J. Pathol., 2000, 192, 97-104).

In a T-cell dependent rat model of experimentally-induced arthritis that mimics many of the clinical features of human rheumatoid arthritis, inhibition of RANKL function through OPG treatment prevents bone destruction (Kong et al., Nature, 1999, 402, 304-309). In a further embodiment of the present invention, RANKL antisense compounds are tested for their ability to prevent osteoclast-mediated bone resorption in a rat model of arthritis.

Female, 12 weeks old, Lewis rats are injected with a single dose of 0.4 mg of heat killed *Mycobacterium tuberculosis* (Difco, Detroit, Mich.) suspended in paraffin oil to induce arthritis. Control animals receive injection of vehicle (paraffin oil) alone. On the same day as the induction of arthritis, both control and bacteria-injected animals receive intraperitoneal injections of saline, 37.5 mg/kg control oligonucleotide or 37.5 mg/kg RANKL antisense oligonucleotide, 2 times per week, for 4 weeks.

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the termination of the study, rats are sacrificed. Femurs are isolated, fixed in 4% formalin, embedded in paraffin, sectioned, stained with hematoxylin and eosin for histological assessment of bone morphology. Sections are cut and stained for the presence of TRAP, a marker of differentiated osteoclasts. Other femur samples are fixed in 4% formalin and subjected to radiographic analysis of bone marrow density. RANKL mRNA levels are measured in bone marrow, proximal tibia and calvaria by real-time PCR.

Example 30

A Parathyroidectomized Rat Model for Bone Resorption

A key mediator of RANKL expression is parathyroid hormone (PTH), a hormone which is synthesized by and secreted from the parathyroid glands in response to changes in extracellular calcium that are detected by a cell-surface calcium-sensing receptor. Increases in serum calcium concentration suppress the release of PTH, whereas decreasing serum calcium stimulates the release of PTH. PTH promotes calcium transport in the gastrointestinal tract and enhances calcium reabsorption in the kidney. Thus, PTH serves an important function as a homeostatic regulator (Rosen and Bilezikian, J. Clin. Endocrinol. Metab., 2001, 86, 957-964; Swarthout et al., Gene, 2002, 282, 1-17).

PTH is also a major regulator of bone remodeling. Continuous infusion of PTH into parathyroidectomized rats causes an increase in RANKL mRNA expression and a decrease in OPG mRNA expression (Ma et al., Endocrinology, 2001, 142, 4047-4054). PTH replacement in thyroparathyroidectomized rats is a well-established in vivo model of controlled bone resorption (Russell et al., Calcif. Tissue Res., 1970, 6, 183-196). Removal of the thryoid and/or parathyroid eliminates the confounding effects of endogenous parathyroid hormone (Ma et al., Endocrinology, 2001, 142, 4047-4054). Since PTH induces osteoclast-mediated bone resorption, this process is inhibited in parathyroidectomized animals. In addition, because PTH mediates calcium reabsorption for the kidneys and absorption from the small intestine, serum calcium is decreased in parathyroidectomized animals, and the animals remain in a hypocalcemic state. Controlled PTH replacement results in serum calcium increase due to PTH-induced osteoclast-mediated bone degradation, thus, serum calcium can be used to measure bone resorption (Swarthout et al., Gene, 2002, 282, 1-17).

In accordance with the present invention, the RANKL antisense compounds are tested in a rat model of PTH-induced bone resorption, to test their ability to inhibit osteoclast activity and consequently prevent bone degradation.

Weanling Sprague Dawley female rats (Harlan, Indianapolis, Ind.) weighing 60-70 g are parathyroidectomized by the vendor before delivery. To minimize the gut and kidney effects on serum calcium, rats are fed a calcium-free diet containing 0.02% Ca, 0.3% P (TD 99171, Teklad, Madison, Wis.) during the experimental period. Synthetic human PTH 1-38 (Zenaca Inc., Wilmington, Del.) 0.01 to 20 µg/100 g/6 h is given by subcutaneous infusion via an Alzet pump (no. 20011, Durect Corp., Palo Alto, Calif.) to the rats for 6 hours. Sham parathyroidectomized rats serve as a control. Both control and parathryoidectomized rats receive intraperitoneal injections of saline, 37.5 mg/kg control oligonucleotide or 37.5 mg/kg RANKL antisense oligonucleotide 2 times per week for two weeks prior to the PTH infusion.

Osteoclast-mediated bone degradation causes a rise in serum calcium levels, thus serum calcium is monitored at intervals throughout the treatment period by collection of blood samples that are analyzed using the Sigma Diagnostics Calcium Kit (Sigma-Aldrich, St. Louis, Mo.). Bone marrow density is monitored throughout the treatment period by x-ray analysis.

At the termination of the study, rats are sacrificed. Femurs are isolated, fixed in 4% formalin, embedded in paraffin, sectioned, stained with hematoxylin and eosin for histological assessment of bone morphology. Sections are cut and stained for the presence of TRAP, a marker of differentiated osteoclasts. Other femur samples are fixed in 4% formalin and subjected to radiographic analysis of bone marrow density. RANKL mRNA levels are measured in bone marrow, proximal tibia and calvaria by real-time PCR.

All references, issued patents and patent applications cited within the body of the instant specification are hereby incorporated by reference in their entirety, for all purposes.

What is claimed is:

1. A method of inhibiting expression of RANKL in bone tissue in an animal, comprising subcutaneously or intraperitonealy administering an effective amount of a compound comprising a modified oligonucleotide consisting of 12 to 50 linked nucleosides targeted to a nucleic acid molecule encoding human RANKL, wherein said modified oligonucleotide is targeted to nucleotides 285-400 of SEQ ID NO: 4, wherein said modified oligonucleotide is at least 90% complementary to SEQ ID NO:4, and wherein said expression of RANKL in said bone tissue is inhibited by at least 35%.

2. The method of claim 1, wherein said compound consists of a single-stranded modified oligonucleotide.

3. The method of claim 2, wherein at least one internucleoside linkage of said modified oligonucleotide is a modified internucleoside linkage.

4. The method of claim 3, wherein each internucleoside linkage of said modified oligonucleotide is a phosphorothioate internucleoside linkage.

5. The method of claim 2, wherein at least one nucleoside of said modified oligonucleotide comprises a modified sugar.

6. The method of claim 5, wherein at least one modified sugar is a bicyclic sugar.

7. The method of claim 5, wherein at least one modified sugar is selected from the group consisting of a 2'-O-(2-methoxyethyl) and a 4'-(CH$_2$)$_n$—O-2' bridge, wherein n is 1 or 2.

8. The method of claim 2, wherein at least one nucleoside of said modified oligonucleotide comprises a modified nucleobase.

9. The method of claim 8, wherein the modified nucleobase is a 5-methylcytosine.

10. The method of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

11. The method of claim 10, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each internucleoside linkage of said modified oligonucleotide is a phosphorothioate linkage, and wherein each cytosine of said modified oligonucleotide is a 5-methylcytosine.

12. The method of claim 2, wherein the modified oligonucleotide consists of 20 linked nucleosides.

13. The method of claim 1, wherein said modified oligonucleotide consists of 15 to 30 linked nucleosides.

14. The method of claim 1, wherein said modified oligonucleotide is at least 95% complementary to SEQ ID NO:4.

15. The method of claim 1, wherein said modified oligonucleotide is 100% complementary to SEQ ID NO:4.

16. The method of claim 11, wherein the modified oligonucleotide consists of 20 linked nucleosides.

* * * * *